United States Patent
Gysling

(10) Patent No.: US 7,661,302 B2
(45) Date of Patent: Feb. 16, 2010

(54) MULTI-PHASE FLOW MEASUREMENT SYSTEM HAVING A FLUID SEPARATOR

(75) Inventor: Daniel L. Gysling, Glastonbury, CT (US)

(73) Assignee: Expro Meters, Inc., Wallingford, CT (US)

( * ) Notice: Subject to any disclaimer, the term of this patent is extended or adjusted under 35 U.S.C. 154(b) by 347 days.

(21) Appl. No.: 11/482,870

(22) Filed: Jul. 7, 2006

(65) Prior Publication Data

US 2007/0006640 A1 Jan. 11, 2007

Related U.S. Application Data

(60) Provisional application No. 60/760,845, filed on Jan. 19, 2006, provisional application No. 60/759,159, filed on Jan. 12, 2006, provisional application No. 60/758,382, filed on Jan. 11, 2006, provisional application No. 60/724,952, filed on Oct. 6, 2005, provisional application No. 60/697,479, filed on Jul. 7, 2005, provisional application No. 60/762,101, filed on Jan. 24, 2006, provisional application No. 60/773,146, filed on Feb. 13, 2006, provisional application No. 60/774,706, filed on Feb. 17, 2006, provisional application No. 60/818,199, filed on Jun. 30, 2006.

(51) Int. Cl.
*G01F 15/08* (2006.01)

(52) U.S. Cl. ...................................................... 73/200
(58) Field of Classification Search .................... 73/200
See application file for complete search history.

(56) References Cited

U.S. PATENT DOCUMENTS

| 4,576,043 | A | 3/1986 | Nguyen et al. |
| 5,551,305 | A | 9/1996 | Farchi et al. |
| 5,741,977 | A | 4/1998 | Agar et al. |

FOREIGN PATENT DOCUMENTS

| GB | 1208121 | 10/1970 |
| WO | WO 0246706 | 6/2002 |

*Primary Examiner*—Rodney T Frank

(57) ABSTRACT

An apparatus for determining a characteristic of a fluid flow within a pipe is provided, wherein the apparatus includes a separating device for separating the fluid into a gas component and a liquid component and directing the gas component to flow within a gas leg portion of the pipe and the liquid component to flow within a liquid portion of the pipe. The apparatus includes a gas leg portion metering device for generating gas component data and a liquid leg portion metering device for generating liquid component data. Moreover, the apparatus includes a processing device communicated with at least one of the gas leg portion metering device and the liquid leg portion metering device, the processing device being configured to receive and process at least one of the gas component data and the liquid component data to generate fluid flow data responsive to a fluid flow characteristic.

14 Claims, 32 Drawing Sheets

Model 1595 over-reading vs. Lockhart-Martinelli
0.4 Beta, with curve fit

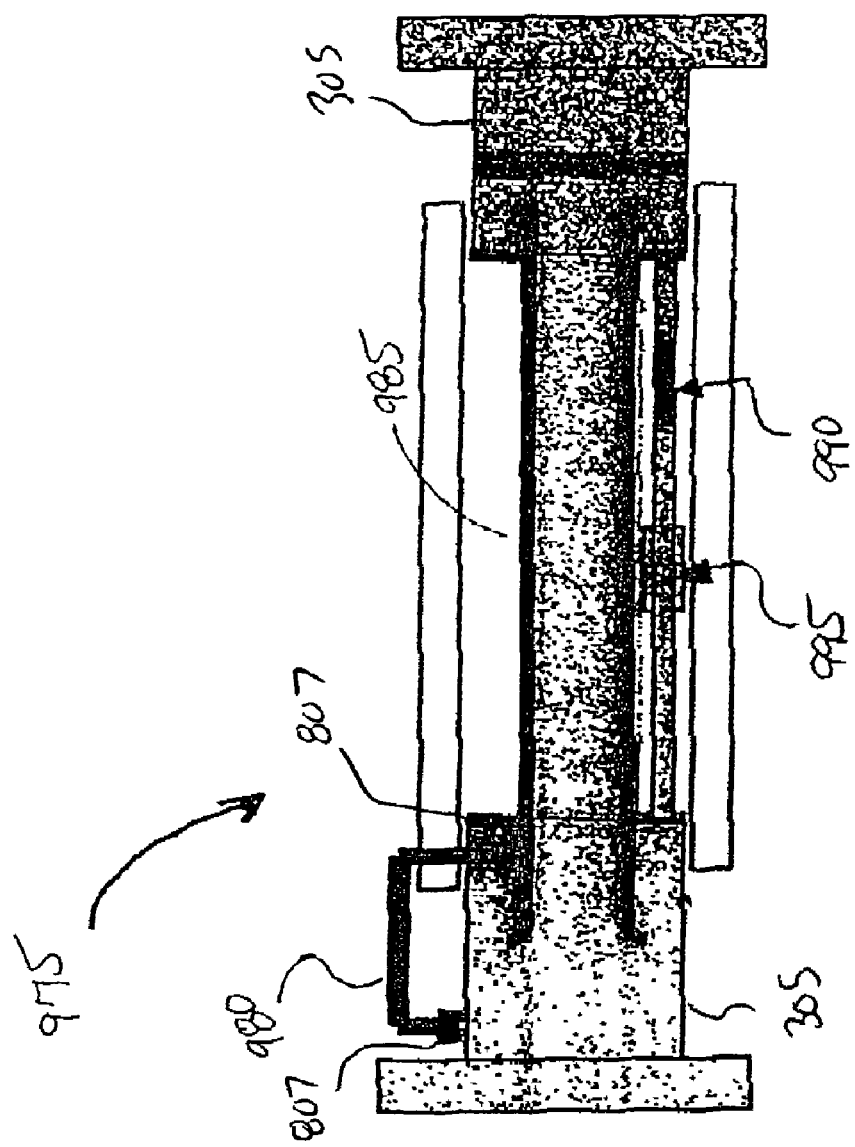

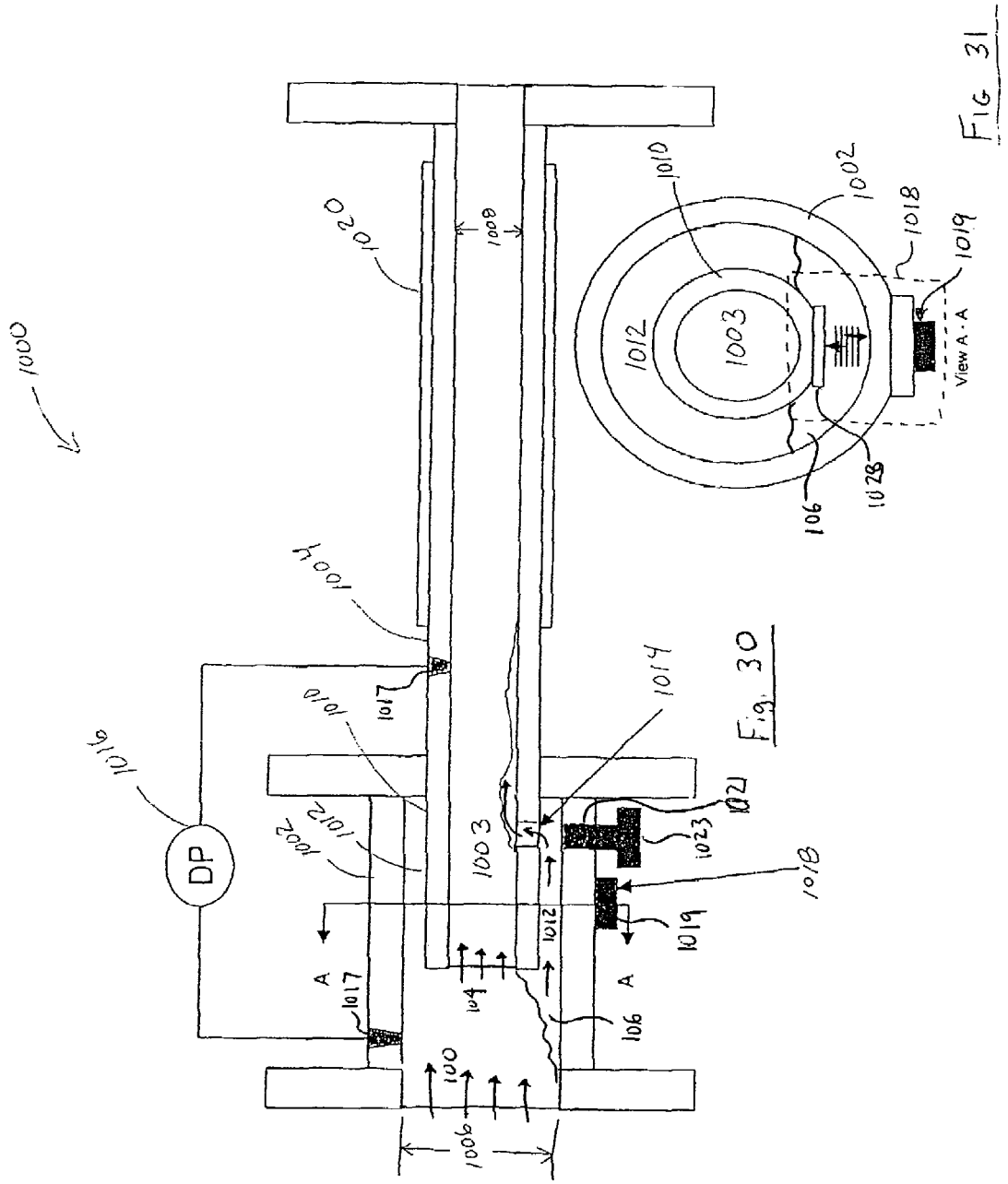

MULTI-PHASE FLOW MEASUREMENT SYSTEM HAVING A FLUID SEPARATOR

CROSS-REFERENCE TO RELATED PATENT APPLICATIONS

This application claims the benefit of U.S. Provisional Patent Application No. 60/760,845 filed Jan. 19, 2006; U.S. Provisional Patent Application No. 60/759,159 filed Jan. 12, 2006; U.S. Provisional Patent Application No. 60/758,382 filed Jan. 11, 2006; U.S. Provisional Patent Application No. 60/724,952 filed Oct. 6, 2005; U.S. Provisional Patent Application No. 60/697,479 filed Jul. 7, 2005; U.S. Provisional Patent Application No. 60/762,101 filed Jan. 24, 2006; U.S. Provisional Patent Application No. 60/773,146 filed Feb. 13, 2006; U.S. Provisional Patent Application No. 60/774,706 filed Feb. 17, 2006; and U.S. Provisional Patent Application No. 60/818,199 filed Jun. 30, 2006, all of which are incorporated by reference herein in their entirety.

BACKGROUND OF THE INVENTION

A fluid flow process (flow process) includes any process that involves the flow of fluid through pipes, ducts, or other conduits, as well as through fluid control devices such as pumps, valves, orifices, heat exchangers, and the like. Flow processes are found in many different industries, such as the oil and gas industry, refining, food and beverage industry, chemical and petrochemical industry, pulp and paper industry, power generation, pharmaceutical industry, and water and wastewater treatment industry. The fluid within the flow process may be a single phase fluid (e.g., gas, liquid or liquid/liquid mixture) and/or a multi-phase mixture (e.g. paper and pulp slurries or other solid/liquid mixtures), wherein the multi-phase mixture may be a two-phase liquid/gas mixture, a solid/gas mixture, a solid/liquid mixture, a gas entrained liquid or a three-phase mixture.

In certain flow processes, such as those found in the oil and gas industries, it is desirable to separate the liquid (e.g., oil and/or water) and gas (e.g., air) components of the fluid. This is typically accomplished using a separator, which is an item of production equipment used to separate the liquid components of the fluid stream from the gaseous components. The liquid and gas components flow from the separator in separate legs (pipes), with the leg containing the gas component referred to as the "gas leg" and the leg containing the liquid component referred to as the "liquid leg". Each of the legs typically includes a flow meter to determine the volumetric flow rate of the gas and fluid components, respectively. Furthermore, for the gas leg, the volumetric flow rate is commonly measured using an orifice plate.

Unfortunately however, current gas/liquid separator devices tend to be large, bulky and inefficient devices that are expensive to implement and operate. For example, current separators require a host of electronic equipment to control the operation of the separation device. This type of sensitive equipment is expensive to maintain. Furthermore, the carry-over of liquid into the gas leg of the gas/liquid separator commonly occurs, wherein the liquid typically takes the form of a mist comprised of small liquid droplets. In order to address this issue, most separators include mist catchers designed to recover the liquid carried over. This tends to increase the size of the already bulky separator devices. Thus, it is an object of the present invention to provide an in-line solution for accurately conducting multi-phase in-line measurements while eliminating the separator device.

SUMMARY OF THE INVENTION

An apparatus for determining a characteristic of a fluid flow within a pipe is provided, wherein the apparatus includes a separator portion for separating the fluid into a gas component and a liquid component and directing the gas component to flow within a gas leg portion of the pipe and the liquid component to flow within a liquid leg portion of the pipe. The apparatus includes a gas leg portion metering device, wherein the gas leg portion metering device generates gas component data responsive to a gas component characteristic and a liquid leg portion metering device, wherein the liquid leg portion metering device generates liquid component data responsive to a liquid component characteristic. Moreover, the apparatus includes a processing device communicated with at least one of the gas leg portion metering device and the liquid leg portion metering device, the processing device being configured to receive and process at least one of the gas component data and the liquid component data to generate fluid flow data responsive to a fluid flow characteristic.

BRIEF DESCRIPTION OF THE DRAWINGS

Referring now to the drawings, the foregoing and other features and advantages of the present invention will be more fully understood from the following detailed description of illustrative embodiments, taken in conjunction with the accompanying drawings in which like elements are numbered alike:

FIG. 29 illustrates a flow meter system having a bypass pipe to separate the fluid flow and measure parameters of a fluid flow including a multiphase fluid flow, in accordance with the present invention.

FIG. 30 is a cross-sectional view of another embodiment of a flow meter system to separate the fluid flow and measure parameters of a fluid flow including a multiphase fluid flow, in accordance with the present invention.

FIG. 31 is a cross-sectional view of the flow meter system of FIG. 30 taken along the line A-A.

DETAILED DESCRIPTION

Differential pressure-based (DP) flow meters are widely used to monitor gas production and are well-known to over-report gas flow rates in the presence of liquids, wherein this tendency to over report due to wetness indicates a strong correlation with the liquid to gas mass ratio of the flow. Additionally, it has been observed that sonar meters, as will be described hereinafter, continue to accurately report gas flow rates, independent of the liquid loading. As such, this insensitivity to wetness provides a practical means for accurately measuring the gas flow rate and the liquid flow rate of a wet gas flow. In the processing of the combined data (i.e. data obtained from the DP meter and the sonar meter) a set of local wetness sensitivity coefficients for each wetness series (at fixed pressure and flow rate) can be used to provide a more accurate characterization for both the DP meter and the sonar meter to determine wetness, wherein the wetness sensitivity coefficients for each device may be provided by a low order polynomial fit of the over-report vs wetness. This characterization may then be used to "invert" the outputs of the DP meter and the sonar meter to provide an accurate gas flow rate and an accurate liquid flow rate. It should be appreciated that the insensitivity of a sonar meter to wetness deteriorates with decreasing densimetric Froude numbers (Fr), wherein the densimetric Froude number is a measure of the degree of "mixedness" in the flow. As is known, the Froude number is given by, $$Fr \equiv \left(\sqrt{\frac{\rho_{gas}}{\rho_{liq}}}\right)\frac{Q_{gas}}{gD}. \quad \text{(Eqn 1)}$$

Wherein Fr is the Froude number, $\rho_{gas}$ is the gas density, $\rho_{liq}$ is the liquid density, $Q_{gas}$ is the flow velocity of the gas and gD is the force of gravity multiplied by the inner diameter of the pipe. It should be appreciated that more accurate results are obtained from flows that are well mixed and the Froude number is a measure of how well the flow is mixed. Thus, the higher the Froude number, the better the flow is mixed. For example, for a Froude number of greater than 2 (i.e. Fr>2), the reported gas rates from the sonar meter are typically within 5% of the actual amount, independent of wetness. It should also be appreciated that flows having a Froude number greater than or equal to two (Fr≧2) tend to produce optimum results.

Figure 1A:
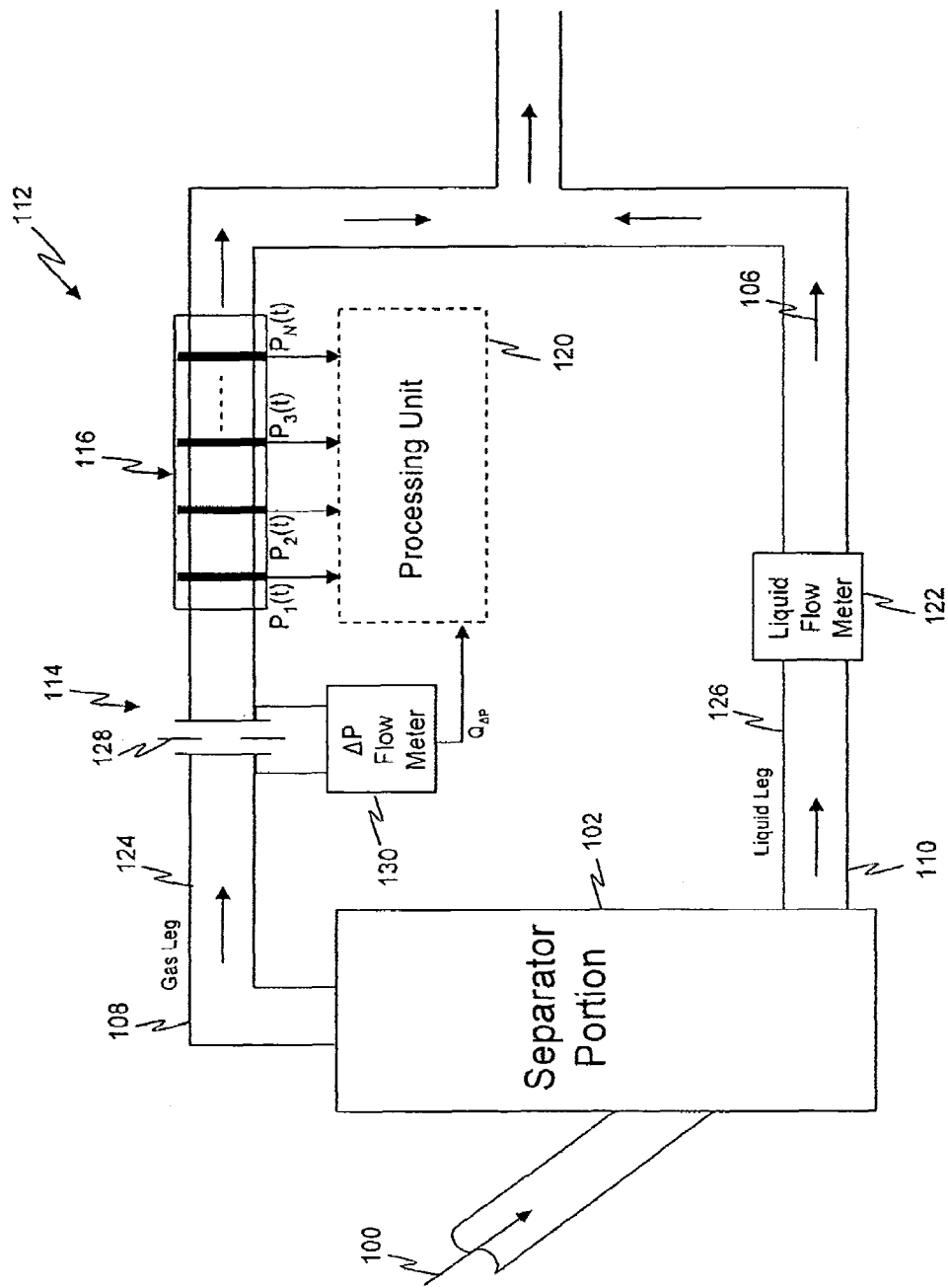
FIG. 1a is general overall schematic diagram of an apparatus for measuring wetness and volumetric flow rate of a gas flow within a pipe.
Figure 1B:
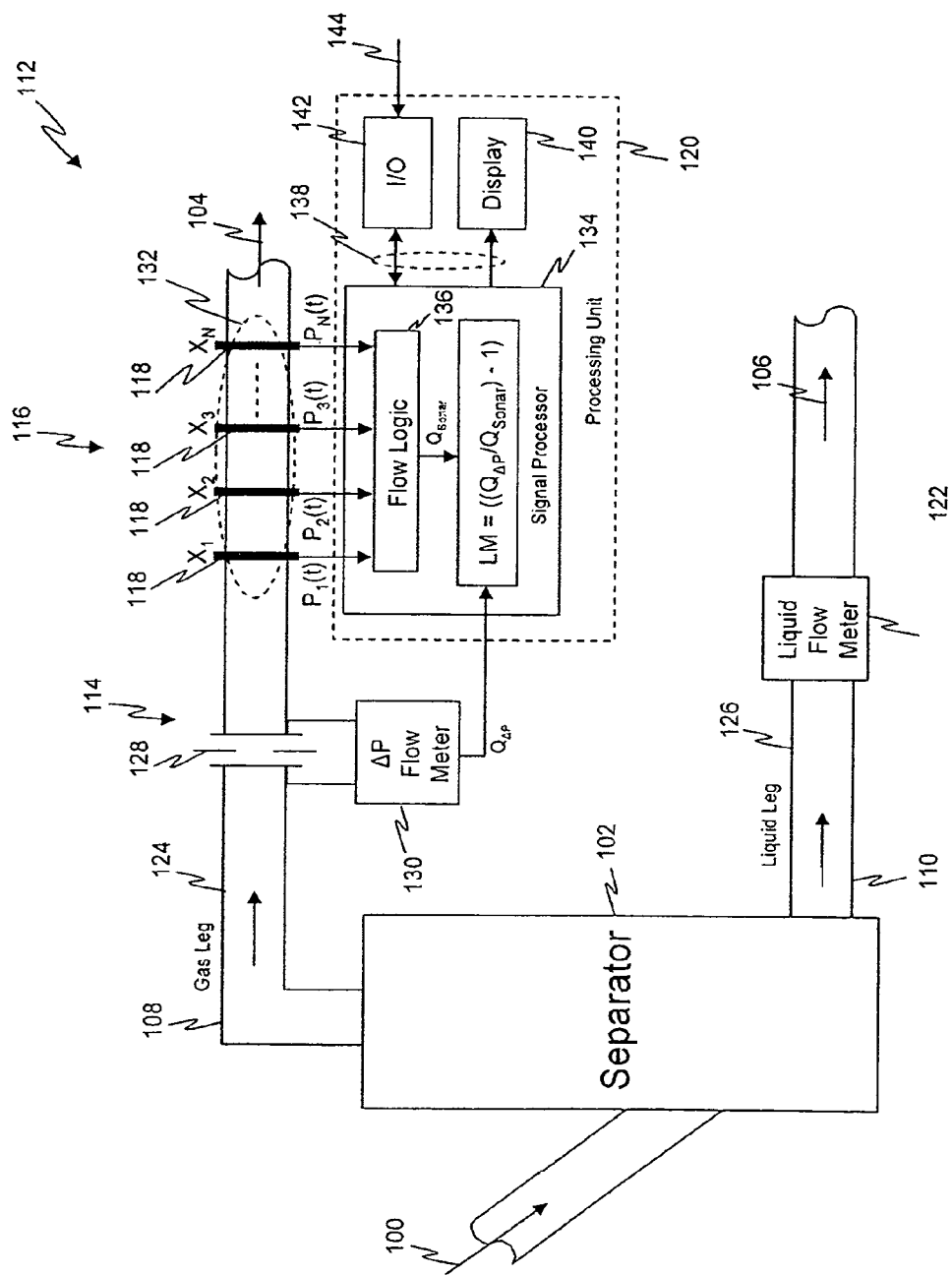
FIG. 1b is general overall schematic diagram of an apparatus for measuring wetness and volumetric flow rate of a gas flow within a pipe

As shown in FIG. 1a and FIG. 1b, a general overall schematic diagram of a system for separating a fluid flow 100 into a gas component 104 and a liquid component 106 is shown. The fluid flow 100 is introduced into a separator portion 102 which separates the fluid flow 100 into the gas mixture 104 and the liquid 106, as will be described in greater detail hereinafter, wherein the gas mixture 104 is directed to flow in a gas leg portion 108 of the separator portion 102 and the liquid 106 is directed to flow in a liquid leg portion 110 of the separator portion 102. The gas mixture 104 flowing in the gas leg 108 includes gas and liquid carry-over from the separator portion 102. An apparatus 112 is provided to measure the wetness and flow rate of the gas mixture 104 and may include a differential flow meter ("DP meter") 114 and a sonar flow meter 116 having an array of strain-based sensors 118, wherein the combination of the DP meter 114 and the sonar flow meter 116 provides flow rate measurements and sensor signals to a separator outflow processor 120. As will be described in greater detail hereinafter, using the measurements from the DP meter 114 and the sonar flow meter 116 the separator outflow processor 120 determines the wetness of the gas mixture 104 in the gas leg 108 as well as, the volumetric flow rate of the gas, and the volumetric flow rate of the liquid carry-over. The volumetric flow rate of the components of the liquid carry-over (i.e. oil and water) may be determined by assuming a known or typical water cut (or phase fraction) or by using the water cut measured as may be provided by a liquid flow meter 122 disposed on the liquid leg portion 110 of the separator portion 102.

Referring again to FIG. 1a and FIG. 1b, the apparatus 112 for measuring wetness and volumetric flow rate of the gas flow 104 within a pipe 124 is shown and includes the differential pressure based flow meter 114 and the sonar based flow meter 116. As will be described in further detail hereinafter, the volumetric flow rate of the gas flow 104 determined by the differential pressure based flow meter 114 ($Q_{\Delta P}$) is used along with the volumetric flow rate of the gas flow 104 determined by the sonar based flow meter 116 ($Q_{sonar}$) to determine the wetness of the gas flow 104, which may be expressed as a Lockhardt Martinelli (LM) number. It should be appreciated that the errors in the interpreted liquid flow rate are generally correctable to a high degree of accuracy provided that the amount of entrained gas is known. Fortunately, from a measurement perspective, the source of the free gas in the liquid leg 110 has no bearing on its effect on the flow measurement and the impact of the free gas scales directly with the gas void fraction. Additionally, it should be appreciated that although in the example shown the pipe 124 is depicted as the gas leg 108 of the gas/liquid separator portion 102, it is contemplated that the apparatus 112 may be used on any duct, conduit or other form of pipe 124 through which a gas 104 may flow.

The gas/liquid separator portion 102 is as described in greater detail hereinafter and may be used to separate liquid components of an incoming fluid stream 100 from any gaseous components. As will also be described in greater detail hereinafter, generally the liquid and gas components flow from the separator portion 102 in separate pipes (legs) 124 and 126, with the leg 124 containing the gas component 104 and the leg 126 containing the liquid component 106, wherein the flow within the leg 124 will be recombined with the flow within the leg 126. The liquid leg 126 may include the liquid flow meter 122, which measures the volumetric flow rate of the liquid 106 flowing there through.

The differential pressure based flow meter 114 may include any type of flow meter that enables flow measurement using a differential pressure ($\Delta P$) in the flow 104. For example, the DP flow meter 114 may enable flow measurement by using a flow obstruction 128 or restriction to create a differential pressure that is proportional to the square of the velocity of the gas flow 104 in the pipe 124, in accordance with Bernoulli's theorem. This differential pressure across the obstruction 128, using a pair of pressure sensors, may be measured and converted into a volumetric flow rate using a processor or secondary device 130, such as a differential pressure transmitter. In the example shown, the flow obstruction 128 is an orifice plate 128 through which the wet gas flow 104 passes. The transmitter 130 senses the drop in pressure of the flow 104 across the orifice plate 128, and determines a volumetric flow rate of the wet gas flow 104 ($Q_{\Delta P}$) as a function of the sensed pressure drop. While an orifice-based flow meter 128 is shown, it will be appreciated that the differential pressure based flow meter 114 may include a venturi meter, an elbow flow meter, a v-cone meter, a pipe constriction or the like.

The sonar based flow meter 116 includes a spatial array 132 of at least two pressure sensors 118 disposed at different axial locations $x_1 \ldots x_N$ along the pipe 124. Each of the pressure sensors 118 provides a pressure signal P(t) indicative of unsteady pressure within the pipe 124 at a corresponding axial location $x_1 \ldots x_N$ of the pipe 124. A signal processor 134 receives the pressure signals $P_1(t) \ldots P_N(t)$ from the pressure sensors 118 in the array 132, and determines the velocity and volumetric flow rate of the wet gas flow 104 using pressure signals from the pressure sensors 118. The signal processor 134 then applies array-processing techniques to the pressure signals $P_1(t) \ldots P_N(t)$ to determine the velocity, volumetric flow rate, and/or other parameters of the wet gas flow 104.

While the sonar based flow meter 116 is shown as including four pressure sensors 118, it is contemplated that the array 132 of pressure sensors 118 may include two or more pressure sensors 118, each providing a pressure signal P(t) indicative of unsteady pressure within the pipe 124 at a corresponding axial location X of the pipe 124. For example, the sonar based flow meter 116 may include 2, 3, 4, 5, 6, 7, 8, 9, 10, 11, 12, 13, 14, 15, 16, 17, 18, 19, 20, 21, 22, 23, or 24 pressure sensors 118. Generally, the accuracy of the measurement improves as the number of sensors 118 in the array 132 increases. The degree of accuracy provided by the greater number of sensors 118 is offset by the increase in complexity and time for computing the desired output parameter of the flow. Therefore, the number of sensors 118 used is dependent at least on the degree of accuracy desired and the desired update rate of the output parameter provided by the meter 116.

The signals $P_1(t) \ldots P_N(t)$ provided by the pressure sensors 118 in the array 132 are processed by the signal processor 134, which may be part of the larger processing unit 120. For example, the signal processor 134 may be a microprocessor and the processing unit 120 may be a personal computer or other general purpose computer. It is contemplated that the signal processor 134 may be any one or more analog or digital signal processing devices for executing programmed instructions, such as one or more microprocessors or application specific integrated circuits (ASICS), and may include memory for storing programmed instructions, set points, parameters, and for buffering or otherwise storing data. Further, it should be appreciated that some or all of the functions within the flow logic 136 may be implemented in software (using a microprocessor or computer) and/or firmware, or may be implemented using analog and/or digital hardware, having sufficient memory, interfaces, and capacity to perform the functions described herein.

To determine the volumetric flow rate $Q_{sonar}$ of the wet gas flow 104, the signal processor 134 applies the data from the pressure sensors 118 to flow logic 136 executed by the signal processor 134. The flow logic 136 is described in further detail hereinafter. It is also contemplated that one or more of the functions performed by the secondary device 130 of the differential pressure flow meter 114 may be performed by the signal processor 134. For example, signals indicative of gas flow pressure upstream and downstream of the orifice 128 may be provided to the signal processor 134, and the signal processor 134 may determine the volumetric flow rate $Q_{\Delta P}$. Using the volumetric flow rate of the wet gas flow 104 determined by the differential pressure based flow meter 114 ($Q_{\Delta P}$) and the volumetric flow rate of the gas flow 104 determined by the sonar based flow meter 116 ($Q_{sonar}$), the signal processor 134 can determine the wetness, the volumetric flow rate of the gas portion, and the volumetric flow rate a the liquid portion of the flow 104.

Figure 2:
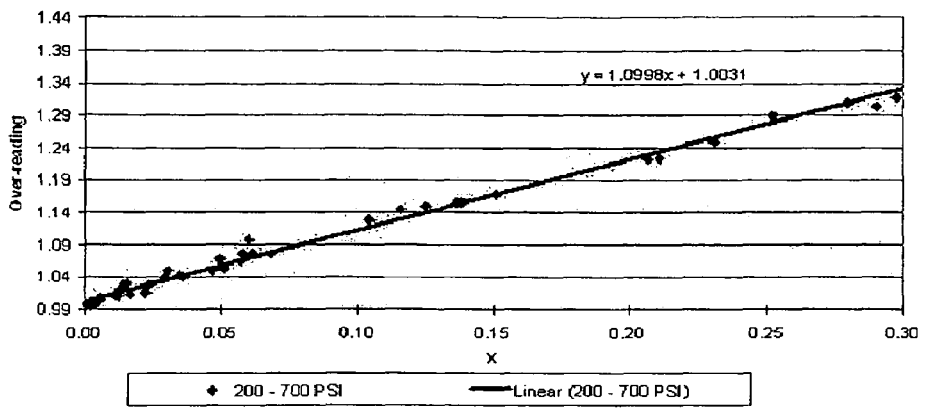
FIG. 2 is a plot of over reporting (over-reading) of an Emerson Model 1595 orifice based flow meter as a function of Lockhart-Martinelli number.

One measure of the wetness of the wet gas flow 104 or a gas continuous mixture is the Lockhardt Martinelli (LM) number. The LM number is defined as the square root of the ratio of the product of liquid mass flow times the liquid volumetric flow to the product of the gas mass flow times the gas volumetric flow and is given by, $$LM \equiv \sqrt{\frac{\dot{m}_{liq} Q_{liq}}{\dot{m}_{gas} Q_{gas}}} \equiv \sqrt{\frac{\rho_{liq} Q_{liq}^2}{\rho_{gas} \rho_{gas}^2}} \equiv \left(\sqrt{\frac{\rho_{liq}}{\rho_{gas}}}\right)\left(\frac{Q_{liq}}{Q_{gas}}\right), \quad \text{(Eqn 2)}$$

wherein, $m_{liq}$ is the liquid mass flow, $Q_{liq}$ is the liquid volumetric flow, $\rho_{liq}$ is the density of the liquid, $m_{gas}$ is the gas mass flow, $Q_{gas}$ is the gas volumetric flow, and $\rho_{gas}$ is the density of the gas. The differential pressure based flow meter 114 will over report the volumetric flow rate of the gas flow 104 by a ratio of $1+\alpha LM$ as compared to the volumetric flow reported for an equivalent volume flow rate of dry gas. FIG. 2 depicts a plot of this over reporting (over-reading) of an Emerson Model 1595 orifice based flow meter as a function of the LM number and as shown, the over reporting scales linearly with the LM number.

Figure 3:
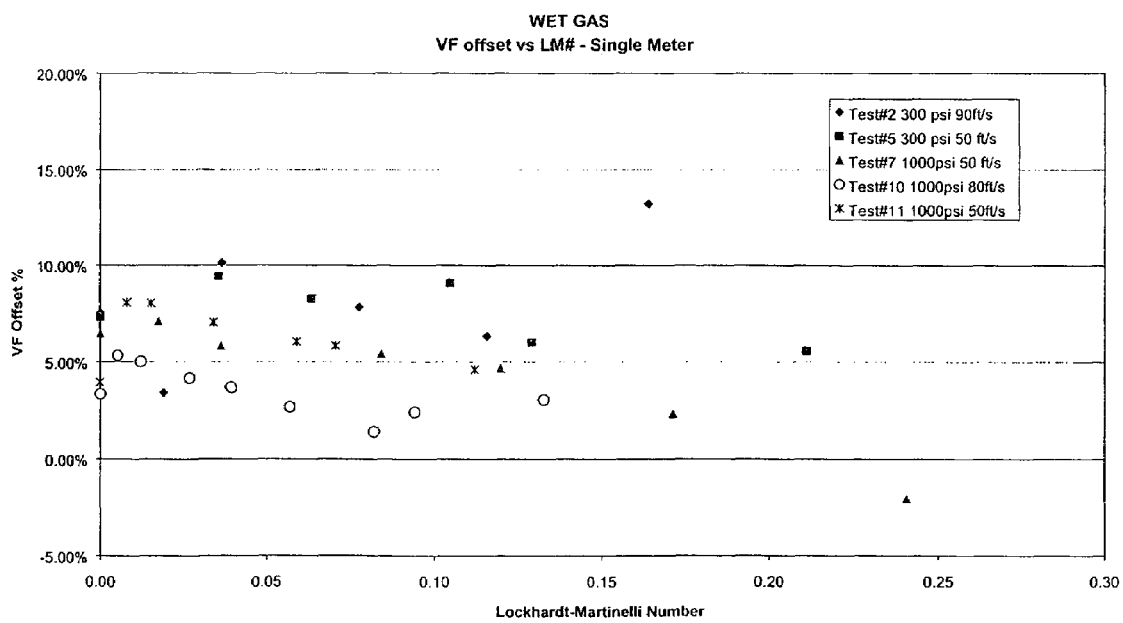
FIG. 3 is a plot depicting the offset between an uncalibrated sonar based volumetric flow meter and a reference volumetric flow rate as a function of Lockhart-Martinelli number.

In contrast, the sonar based volumetric flow meter 116 has been demonstrated to accurately report a volumetric flow of a wet gas mixture with little sensitivity to wetness. FIG. 3 depicts the offset between a sonar flow meter 116 and a reference volumetric flow rate as a function of the LM number. As shown, the offset is a relatively weak function of the LM number. Accordingly:

$$Q_{SONAR} = Q_{gas}, \quad \text{(Eqn 3)}$$

wherein $Q_{SONAR}$ is the flow rate of the gas of the flow 104.

The sonar flow meter 116 and the differential flow meter ("DP meter") 114 will report the same flow rates for dry gases, and will report diverging flow rates with increasing wetness. Thus, the combination of the volumetric flow rates $Q_{\Delta P}$ and $Q_{sonar}$ from the differential pressure based flow meter 114 and sonar based flow meter 116 provide a measure of both the flow rate and the wetness of a gas continuous flow 104, which can be determined by the signal processor 134 using the equations:

$$Q_{\Delta P} = Q_{gas}(1 + \alpha LM) \quad \text{(Eqn 4a)}$$

or $$LM = \frac{1}{\alpha}\left(\frac{Q_{\Delta P}}{Q_{SONAR}} - 1\right) \quad \text{(Eqn 4b)}$$

where $\alpha$ is an empirically determined wetness sensitivity coefficient that may be introduced by various factors, such as environmental factors (i.e. temperature and/or pressure) and/ or factors related to the meter being used (i.e. a characteristic of an individual or group of meters and/or the tolerance of the meter). It should be appreciated that a calibration point can be added by equating the outputs of the differential pressure based flow meter 114 and sonar based flow meter 116 during flow conditions where the gas is known to be dry.

As one can appreciate the LM may be determined using the measured volumetric flow rates (i.e., $Q_{\Delta P}$ and $Q_{SONAR}$) measured by the DP flow meter 114 and the sonar flow meter 116, respectively, using Eqn. 4 b. Knowing the LM number and the density of the gas and liquid, the volumetric flow rate of the liquid may be determined using Eqn. 2 and Eqn. 3.

While the over-reporting may be defined as the linear equation $1+\alpha LM$, one will appreciate that the invention contemplates that the over-reporting can be defined as any function suitable to the desired end purpose, such as a linear, quadratic, polynomial and/or logarithmic function that defines an over-reporting characteristic of the meters which will be described in greater detail hereinafter. In other words, any over-reporting function may be used that accurately fits the output of the flow meters 114, 116 over the desired range of LM numbers (e.g., curve fitting).

The signal processor 134 may output the LM number, the volumetric flow rates $Q_{\Delta P}$ and/or $Q_{sonar}$, velocity of the gas and liquid portions, or any combination thereof, as well as various other parameters that may be determined from these values as a signal 138. The signal 138 may be provided to a display 140, another input/output (I/O) device 142 or another processing device for further processing. Moreover, the I/O device 142 may also accept user input parameters 144 as may be necessary for the flow logic 136. The I/O device 142, display 140, and/or signal processor 134 unit may be mounted in a common housing, which may be attached to the array 132 by a flexible cable, wireless connection, or the like. The flexible cable may also be used to provide operating power from the processing unit 120 to the array 132 if necessary.

Figure 5A:
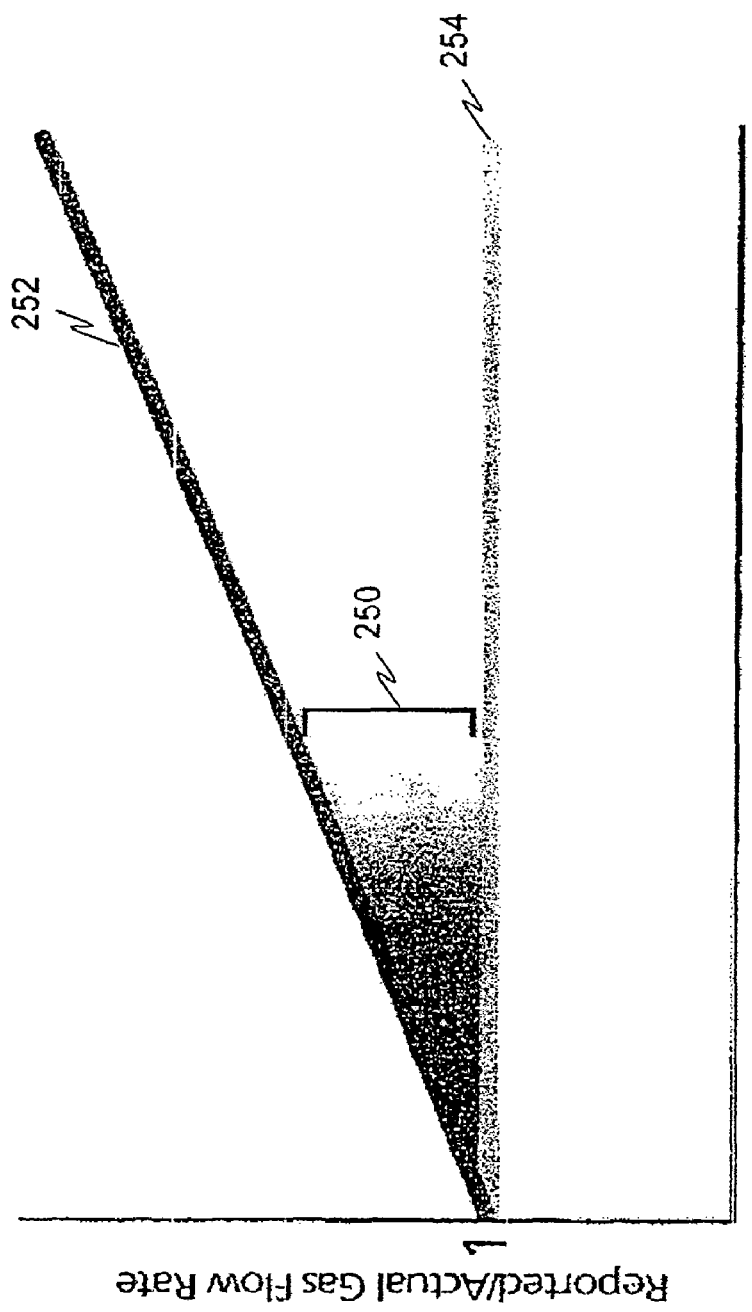
FIG. 5a is plot of the output of a DP meter and an output of a sonar meter to illustrate that the wetness of the gas is relative to the difference of the two outputs in accordance with the present invention.

It should be appreciated that the relationship of the LM number to the output of the DP flowmeter 114 ($Q_{\Delta P}$) and the sonar flow meter 116 ($Q_{SONAR}$) as described hereinbefore is graphically illustrated in FIG. 5a. As shown, the difference 250 between the volumetric flow rate 252 of the DP flowmeter 114 and the volumetric flow rate 254 of the sonar meter 116 is related to the wetness of the gas flow 104 and is given by $1+\alpha LM$. While the description for the sonar meter 116 provides an output signal representative of the velocity or flow rate of the gas to be used in the determination of the wetness, the invention contemplates that any other output of the sonar meter 116, which is insensitive to wetness may be used to determine the wetness of the gas.

Figure 4:
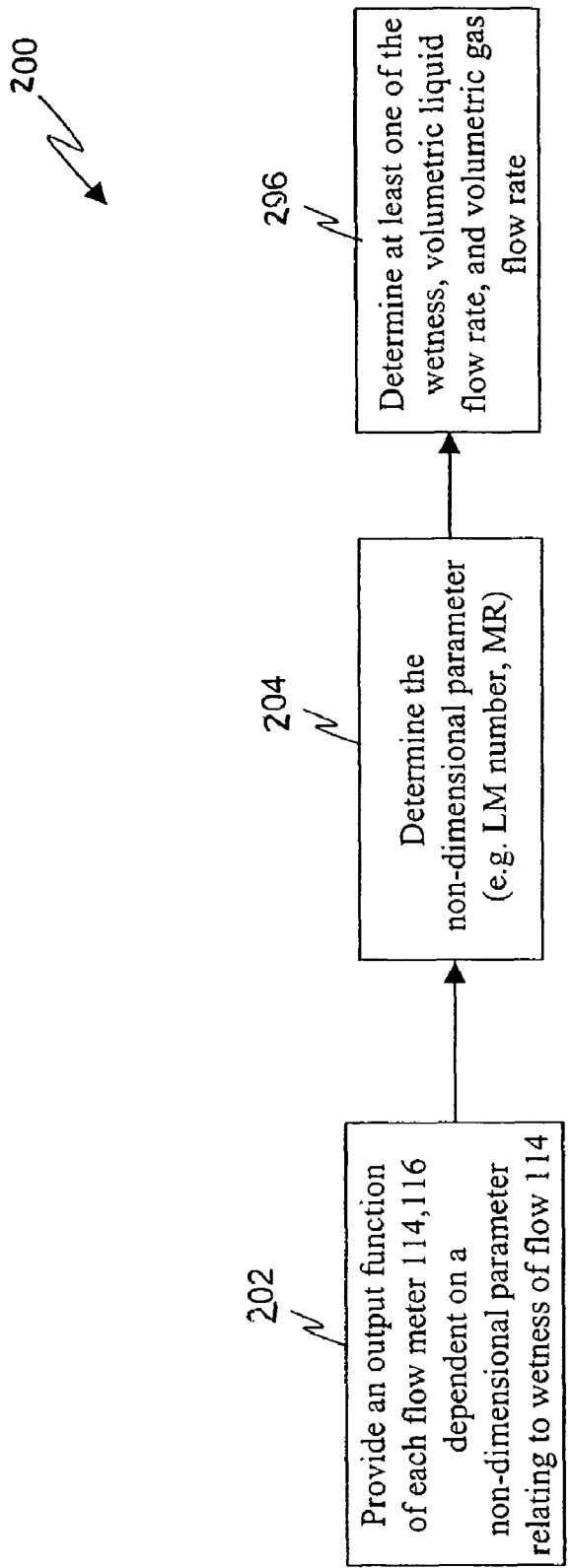
FIG. 4 is a block diagram illustrating one embodiment of a wet gas algorithm in accordance with the present invention.

Referring to FIG. 4, a block diagram 200 describes an algorithm for determining at least one of the wetness, volumetric liquid flow rate, and volumetric gas flow rate of the wet gas 104 flowing in the pipe 124. An output function of each of the flow meters 114, 116 is provided that is dependent on a non-dimensional parameter relating to the wetness of the flow 104, as shown in operational block 202. The non-dimensional parameter (e.g. LM number and liquid to gas mass flow ratio (MR)) is determined, as shown in operational block 204. Knowing the non-dimensional parameter, the gas and liquid volumetric flow rates ($Q_{\Delta P}$, $Q_{SONAR}$) are determined, as shown in operational block 206. This may be accomplished by utilizing the relationship between the volumetric flow rate or velocity of the flow obtained by the sonar flow meter, $Q_{SONAR}$, and the volumetric flow rate or velocity of the flow obtained by the DP flow meter, $Q_{venturi}$, wherein the volumetric flow rate of the wet gas flow 104 obtained by the sonar flow meter, $Q_{SONAR}$, can be expressed as, $$Q_{SONAR} = (1+\alpha MR)Q_{gas}, \quad \text{(Eqn 5)}$$

and the volumetric flow rate of the flow obtained by the Venturi meter, $Q_{venturi}$, can be expressed as, $$Q_{venturi} = (1+\beta MR+\chi MR^2)Q_{gas}, \quad \text{(Eqn 6)}$$

where $\alpha$, $\beta$ and $\chi$ are empirically determined wetness sensitivity coefficients, MR is the liquid to gas mass flow ratio and $Q_{gas}$ is the volumetric flow rate of the gas portion of the wet gas flow 104. While the over-reporting of the sonar meter may be defined as $1+\alpha MR$ and the over-reporting of the DP meter (e.g., venturi meter) may be defined as $1+\beta MR+\chi MR^2$, one will appreciate that the invention contemplates that the over-reporting can be defined as any function suitable to the desired end purpose, such as a linear, quadratic, polynomial and/or logarithmic function that defines an over-reporting characteristic of the meters which will be described in greater detail hereinafter. Moreover, while $Q_{SONAR}$ is shown as being defined by the function in Eqn. 5 and $Q_{venturi}$ is shown as being defined by the function in Eqn. 6, it should be appreciated that $Q_{SONAR}$ and $Q_{venturi}$ may be defined by any function suitable to the desired end purpose, such as a linear, quadratic, polynomial and/or logarithmic function that defines an over-reporting characteristic of the meter(s) as will be described in greater detail hereinafter. In other words, any over-reporting function may be used that accurately fits the output of the flow meters 114, 116 over the desired range of MRs (e.g., curve fitting).

The value for MR may be determined by solving the above equations (Eqn 5 and Eqn 6) for $Q_{gas}$ and equating the two resultant equations as follows, $$Q_{gas} = \frac{Q_{SONAR}}{(1+\alpha MR)}, \quad \text{(Eqn 7)}$$

and $$Q_{gas} = \frac{Q_{venturi}}{(1+\alpha MR+\chi MR^2)}. \quad \text{(Eqn 8)}$$

Thus, it follows that, $$\frac{Q_{SONAR}}{(1+\alpha MR)} = \frac{Q_{venturi}}{(1+\alpha MR+\chi MR^2)}, \quad \text{(Eqn 9)}$$

and, therefore, $$MR = \frac{-\left(\beta-\alpha\frac{Q_{venturi}}{Q_{sonar}}\right)+\sqrt{\left(\beta-\alpha\frac{Q_{venturi}}{Q_{sonar}}\right)^2-4\chi\left(1-\frac{Q_{venturi}}{Q_{sonar}}\right)}}{2\chi}. \quad \text{(Eqn 10)}$$

At this point, the gas flow rate, $Q_{gas}$, and the liquid flow rate, $Q_{Liq}$, can be determined by using the following relationships, $$Q_{gas} = \frac{Q_{SONAR}}{(1+\alpha MR)}, \quad \text{(Eqn 11)}$$

and $$Q_{liq} = \left(\frac{\rho_{gas}}{\rho_{liq}}MR\right)Q_{gas}, \quad \text{(Eqn 12)}$$

where $\rho_{gas}$ is the density of the gas flow and $\rho_{liq}$ is the density of the liquid flow.

Figure 5B:
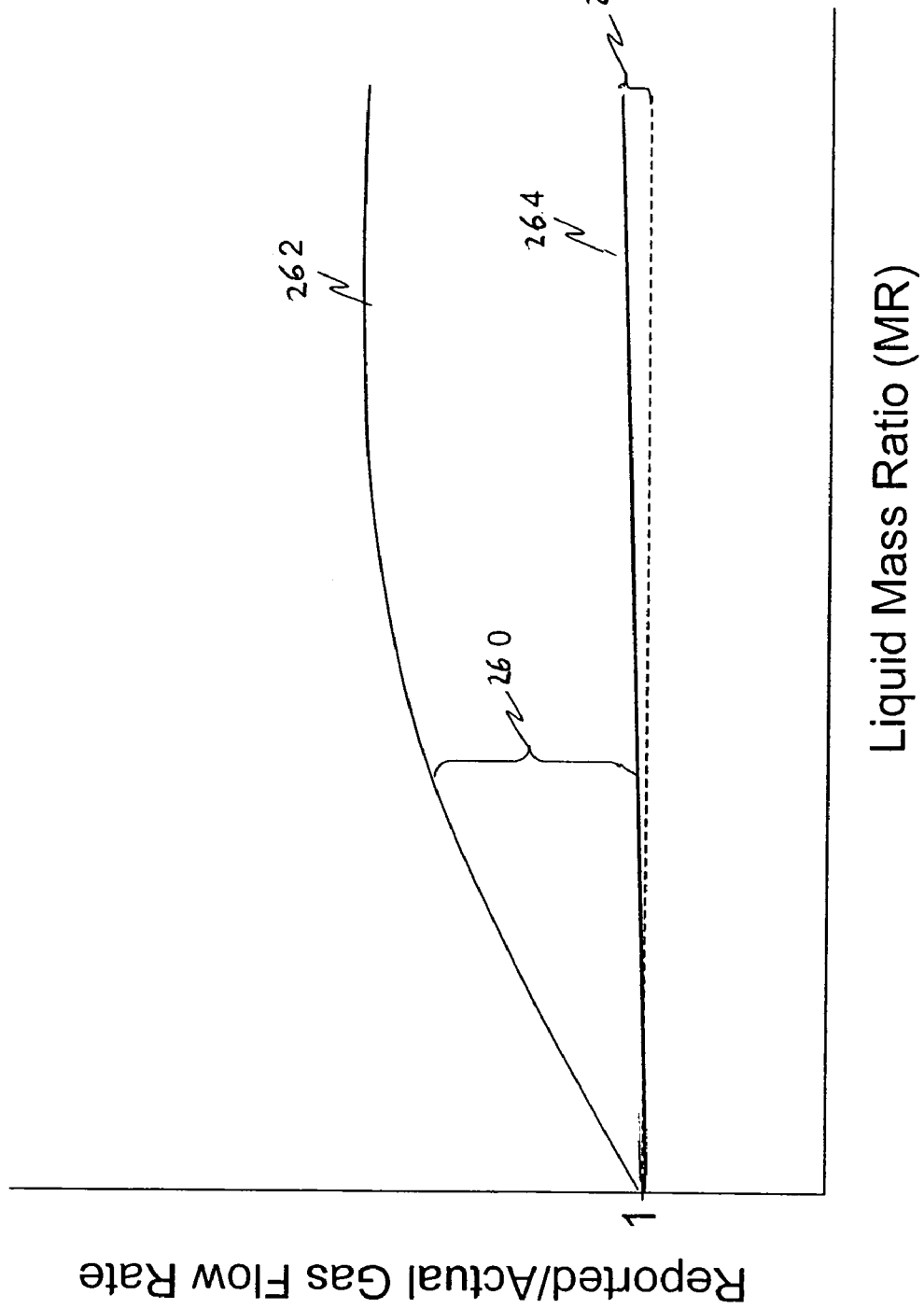
FIG. 5b is a plot of the output of a DP meter and an output of a sonar meter to illustrate that the wetness of the gas is relative to the difference of the two outputs in accordance with the present invention.

It should be appreciated that the relationship of the MR Number to the output of the DP flowmeter 114 ($Q_{\Delta P}$) and the sonar meter 116 ($Q_{SONAR}$) as described hereinbefore is graphically illustrated in FIG. 5b. As shown, the difference 260 between the volumetric flow rate 262 of the DP flowmeter 114 and the volumetric flow rate 264 of the sonar meter 116 is relative to the wetness of the gas flow 104 and is given by $1+\beta MR+\chi MR^2$. While the description for the sonar flow meter 116 provides an output signal representative of the velocity or volumetric flow rate of the gas to be used in the determination of the wetness, the invention contemplates that any other output of the sonar flow meter 116, which is insensitive to wetness may be used to determine the wetness of the gas. Additionally, while the DP flowmeter 114 is described herein as being a venturi meter, the invention contemplates that any other type of DP flowmeter suitable to the desired end purpose may be used.

One will also appreciate that while the characteristics of the output was defined as the volumetric flow rates of the meters, the present invention contemplates that the characteristics may be defined by any other output measured by the flow meters, such as the flow velocity, provided the sensitivity of the outputs to wetness are comparable to the sensitivity of the measured volumetric flow rate. In other words, the measured parameter of the DP flow meter 114 is sensitive to wetness and the measured output of the sonar flow meter 116 is relatively insensitive to wetness of the flow 104.

Furthermore, while the present invention defines the outputs of the DP flow meter 114 and the sonar flow metere 116 as a respective formula to be solved, it will be appreciated that the data may be provided in the form of a look-up table to provide a number for a non-dimensional parameter (e.g., LM number, MR), the volumetric liquid flow rate and volumetric gas flow rate of the flow 104 in response to the measured parameters (velocity, volumetric flow) of the flow meters 114, 116.

Referring to FIG. 1b, the apparatus 112 is shown wherein the wet gas mixture 104 is directed to flow in a gas leg portion 108 of a separator portion 102 and the liquid 106 is directed to flow in a liquid leg portion 110 of the separator portion 102. The gas mixture 104 flowing in the gas leg 108 includes gas and liquid carry-over from the separator portion 102. The fluid flow 100 is shown being introduced into a separator 102 which separates the fluid flow 100 into a gas mixture 104 and a liquid 106, wherein the gas mixture 104 is directed to flow in a gas leg portion 108 of the separator portion 102 and the liquid 106 is directed to flow in a liquid leg portion 110 of the separator portion 102. The gas mixture 104 flowing in the gas leg 108 includes gas and liquid carry-over from the separator portion 102. An apparatus 112 is provided to measure the wetness and flow rate of the gas mixture 104 and may include a differential flow meter ("DP meter") 114 and a sonar flow meter 116 having an array of strain-based sensors 118, wherein the combination of the DP meter 114 and the sonar flow meter 116 provides flow rate measurements to a separator outflow processor 120. As described in greater detail hereinbefore, using the measurements from the DP meter 114 and the sonar flow meter 116, the separator outflow processor 120 determines the wetness of the gas mixture 104 in the gas leg 108 as well as, the volumetric flow rate of the gas, and the volumetric flow rate of the liquid carry-over. The volumetric flow rate of the components of the liquid carry-over (i.e. oil and water) may be determined by assuming a known or typical water cut (or phase fraction) or by using the water cut measured as may be provided by a liquid flow meter 122 disposed on the liquid leg portion 110 of the separator portion 102.

The gas/liquid separator portion 102 is an item of production equipment used to separate liquid components of an incoming fluid stream 100 from any gaseous components. The liquid and gas components flow from the separator portion 102 in separate pipes (legs) 124 and 126, with the leg 124 containing the gas component 104 and the leg 126 containing the liquid component 106. The liquid leg 126 may include the liquid flow meter 122, which measures the volumetric flow rate of the liquid 106 flowing there through. While the separator portion 102 is depicted as a vertical vessel, the gas/liquid separator portion 102 may be any device for separating gas from one or more liquids. For example, the separator portion 102 may include a cylindrical or spherical vessel, and may be either horizontally or vertically positioned. Furthermore, the separator portion 102 may use gravity segregation, centrifugal separation, cyclone separation, or any other known means to accomplish the separation, and may include one or more stages.

It should be appreciated that the sonar flow meter 116 may comprise a plurality of ultrasonic sensors 118 to provide an output signal, for example a velocity measurement. The ultrasonic sonar flow meter 116 is similar to that described in U.S. patent application Ser. No. 10/756,977 filed on Jan. 13, 2004 and U.S. patent application Ser. No. 10/964,043 filed on Oct. 12, 2004, which are incorporated herein by reference.

It should be further appreciated that the sensors 118 may also include electrical strain gages, optical fibers and/or gratings, ported sensors, ultrasonic sensors, among others as described herein, and may be attached to the pipe 124 by adhesive, glue, epoxy, tape or other suitable attachment means to ensure suitable contact between the sensor and the pipe 124. Additionally, the sensors 118 may alternatively be removable or permanently attached via known mechanical techniques such as mechanical fastener, spring loaded, clamped, clam shell arrangement, strapping or other equivalents. Alternatively, strain gages, including optical fibers and/or gratings, may be embedded in a composite pipe 124. If desired, for certain applications, gratings may be detached from (or strain or acoustically isolated from) the pipe 124 if desired. It is also contemplated that any other strain sensing technique may be used to measure the variations in strain in the pipe 124, such as highly sensitive piezoelectric, electronic or electric, strain gages attached to or embedded in the pipe 124.

In various embodiments of the present invention, a piezoelectronic pressure transducer may be used as one or more of the pressure sensors 118 and it may measure the unsteady (or dynamic or ac) pressure variations inside the pipe 124 by measuring the pressure levels inside the pipe 124. In one embodiment of the present invention, the sensors 118 comprise pressure sensors manufactured by PCB Piezotronics of Depew, N.Y. For example, in one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems. It has the unique capability to measure small pressure changes of less than 0.001 psi under high static conditions. The 106B has a 300 mV/psi sensitivity and a resolution of 91 dB (0.0001 psi). The sensors 118 may incorporate a built-in MOSFET microelectronic amplifier to convert the high-impedance charge output into a low-impedance voltage signal. The sensors 118 may be powered from a constant-current source and can operate over long coaxial or ribbon cable without signal degradation. The low-impedance voltage signal is not affected by triboelectric cable noise or insulation resistance-degrading contaminants. Power to operate integrated circuit piezoelectric sensors generally takes the form of a low-cost, 24 to 27 VDC, 2 to 20 mA constant-current supply.

Most piezoelectric pressure sensors are constructed with either compression mode quartz crystals preloaded in a rigid housing, or unconstrained tourmaline crystals. These designs give the sensors microsecond response times and resonant frequencies in the hundreds of kHz, with minimal overshoot or ringing. Small diaphragm diameters ensure spatial resolution of narrow shock waves. The output characteristic of piezoelectric pressure sensor systems is that of an AC-coupled system, where repetitive signals decay until there is an equal area above and below the original base line. As magnitude levels of the monitored event fluctuate, the output remains stabilized around the base line with the positive and negative areas of the curve remaining equal. Furthermore it is contemplated that each of the sensors 118 may include a piezoelectric sensor that provides a piezoelectric material to measure the unsteady pressures of the flow 104. The piezoelectric material, such as the polymer, polarized fluoropolymer, PVDF, measures the strain induced within the process pipe 124 due to unsteady pressure variations within the flow 104. Strain within the pipe 124 is transduced to an output voltage or current by the attached piezoelectric sensors 118.

The PVDF material forming each piezoelectric sensor 118 may be adhered to the outer surface of a steel strap that extends around and clamps onto the outer surface of the pipe 124. The piezoelectric sensing element is typically conformal to allow complete or nearly complete circumferential measurement of induced strain. The sensors can be formed from PVDF films, co-polymer films, or flexible PZT sensors, similar to that described in "Piezo Film Sensors technical Manual" provided by Measurement Specialties, Inc. of Fairfield, N.J., which is incorporated herein by reference. The advantages of this technique are the following:

1. Non-intrusive flow rate measurements;
2. Low cost;
3. Measurement technique requires no excitation source. Ambient flow noise is used as a source;
4. Flexible piezoelectric sensors can be mounted in a variety of configurations to enhance signal detection schemes. These configurations include a) co-located sensors, b) segmented sensors with opposing polarity configurations, c) wide sensors to enhance acoustic signal detection and minimize vortical noise detection, d) tailored sensor geometries to minimize sensitivity to pipe modes, e) differencing of sensors to eliminate acoustic noise from vortical signals; and
5. Higher Temperatures (140 C) (co-polymers).

Flow Logic

Velocity Processing

As described in commonly-owned U.S. Pat. No. 6,609,069 to Gysling, entitled "Method and Apparatus for Determining the Flow Velocity Within a Pipe", which is incorporated herein by reference in its entirety, the unsteady pressures along a pipe 124 caused by coherent structures (e.g., turbulent eddies and vortical disturbances) that convect with a fluid (e.g., gas flow 104) flowing in the pipe 124, contain useful information regarding parameters of the fluid.

Figure 6:
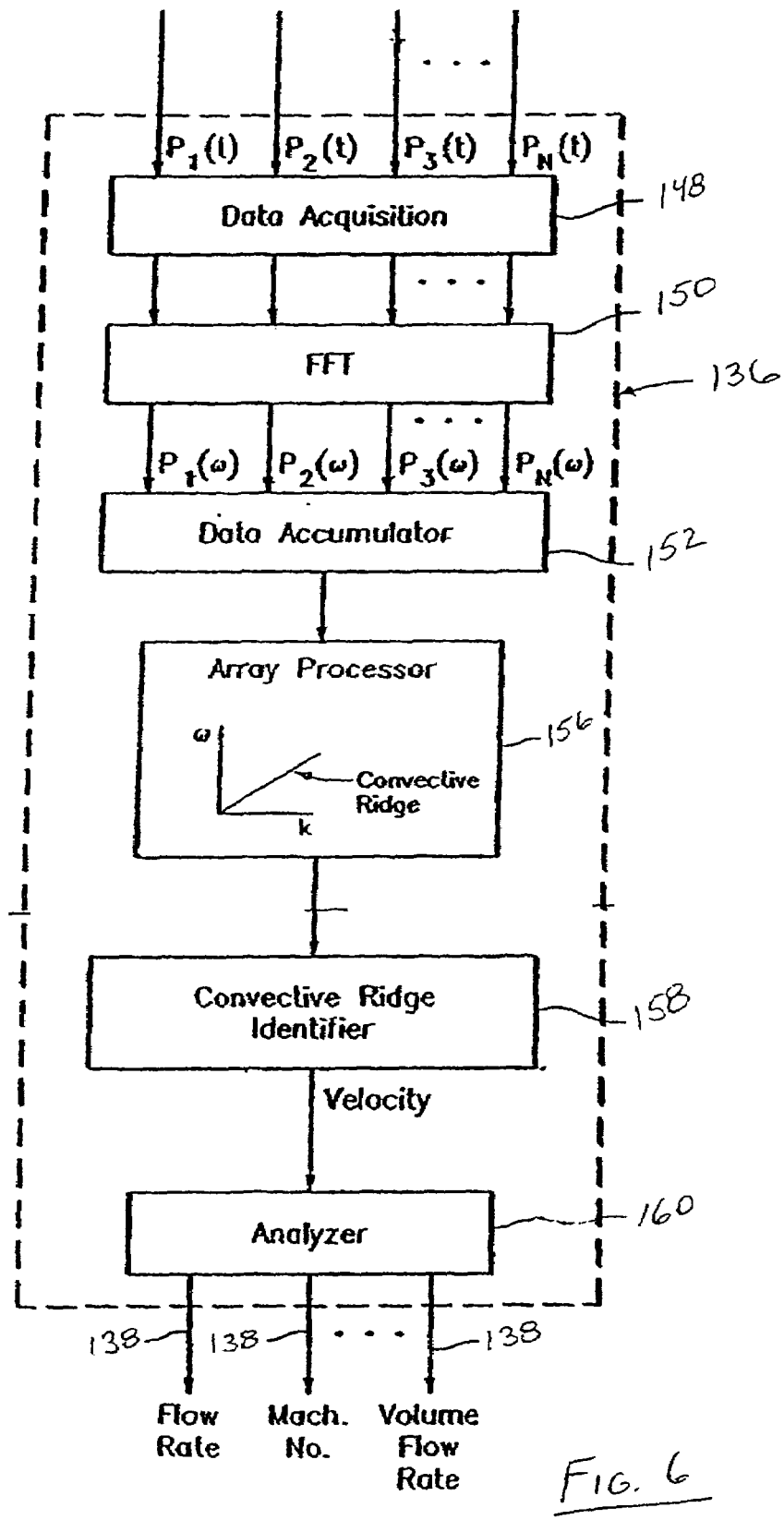
FIG. 6 is a block diagram of a first embodiment of a flow logic used in the apparatus of the present invention.
Figure 7:
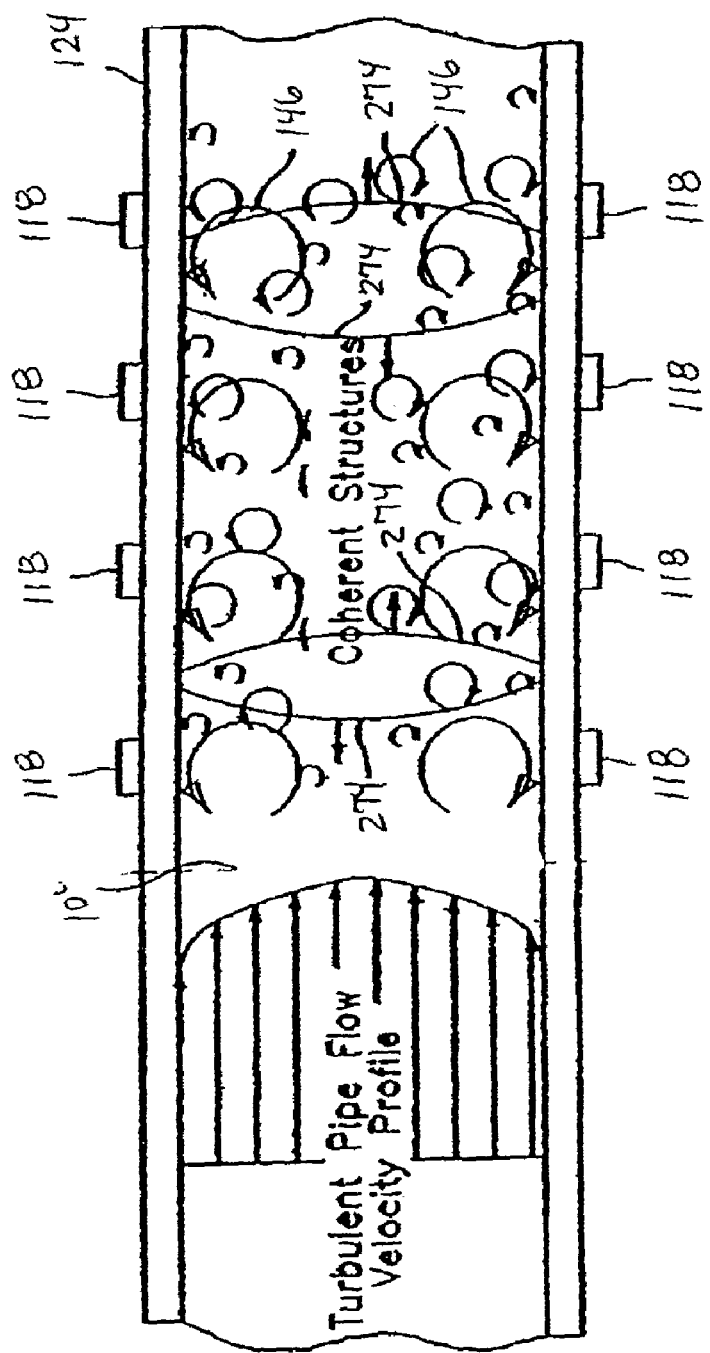
FIG. 7 is a cross-sectional view of a pipe having coherent structures therein.

Referring to FIG. 6, an example of the flow logic 136 is shown. As previously described, the array 132 of at least two sensors 118 located at two locations $x_1$, $x_2$ axially along the pipe 124 sense respective stochastic signals propagating between the sensors 118 within the pipe 124 at their respective locations. Each sensor 118 provides a signal indicating an unsteady pressure at the location of each sensor 118, at each instant in a series of sampling instants. One will appreciate that the array 132 may include more than two sensors 118 distributed at locations $x_1 \ldots x_N$. The pressure generated by the convective pressure disturbances (e.g., eddies 146, see FIG. 7) may be measured through the sensors 118, which may be strained-based sensors and/or pressure sensors. The sensors 118 provide analog pressure time-varying signals $P_1(t)$, $P_2(t)$, $P_3(t) \ldots P_N(t)$ to the signal processor 134, which in turn applies these signals $P_1(t)$, $P_2(t)$, $P_3(t) \ldots P_N(t)$ to the flow logic 136. The flow logic 136 processes the signals $P_1(t)$, $P_2(t)$, $P_3(t) \ldots P_N(t)$ to first provide output signals (parameters) indicative of the pressure disturbances that convect with the fluid (gas) 104, and subsequently, provide output signals in response to pressure disturbances generated by convective waves propagating through the fluid 104, such as velocity, Mach number and volumetric flow rate of the fluid 104.

The signal processor 134 includes data acquisition unit 148 (e.g., A/D converter) that converts the analog signals $P_1(t) \ldots P_N(t)$ to respective digital signals and provides the digital signals $P_1(t) \ldots P_N(t)$ to FFT logic 150. The FFT logic 150 calculates the Fourier transform of the digitized time-based input signals $P_1(t) \ldots P_N(t)$ and provides complex frequency domain (or frequency based) signals $P_1(\omega), P_2(\omega), P_3(\omega), \ldots P_N(\omega)$ indicative of the frequency content of the input signals to a data accumulator 152. Instead of FFTs, any other technique for obtaining the frequency domain characteristics of the signals $P_1(t)$-$P_N(t)$, may also be used. For example, the cross-spectral density and the power spectral density may be used to form one or more frequency domain transfer functions (or frequency responses or ratios) discussed hereinafter. One technique of determining the convection velocity of the turbulent eddies 146 within the fluid 104 is by characterizing a convective ridge (154 in FIG. 8) of the resulting unsteady pressures using an array of sensors or other beam forming techniques, similar to that described in U.S. Pat. No. 6,889,562 and U.S. patent application Ser. No. 09/729,994, U.S. Pat. No. 6,609,069, which are incorporated herein by reference.

Figure 8:
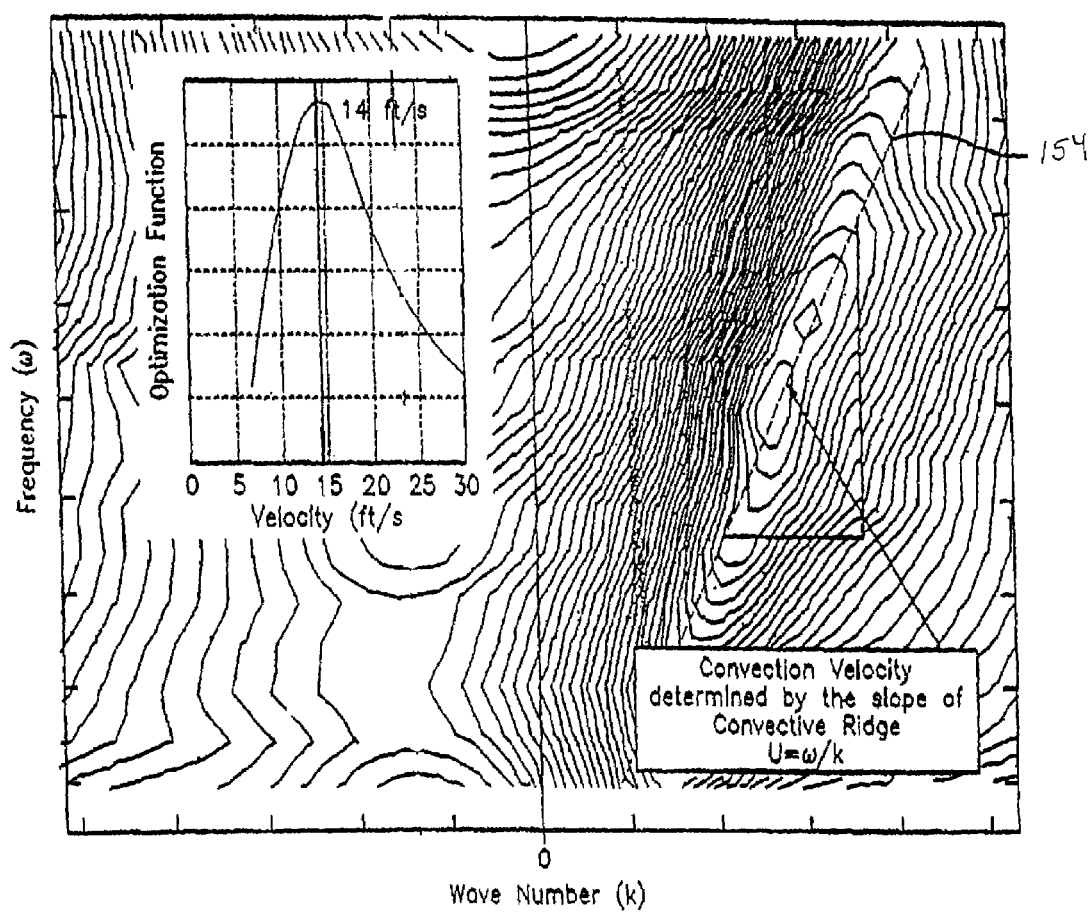
FIG. 8 is a k-ω plot of data processed from the apparatus of FIG. 1 that illustrates slope of the convective ridge, and a plot of the optimization function of the convective ridge.

The data accumulator 152 accumulates the frequency signals $P_1(\omega)$-$P_N(\omega)$ over a sampling interval, and provides the data to an array processor 156, which performs a spatial-temporal (two-dimensional) transform of the sensor data, from the xt domain to the k-ω domain, and then calculates the power in the k-ω plane, as represented by the k-ω plot shown in FIG. 8. The array processor 156 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$ where $\lambda$ is the wavelength of a spectral component, and corresponding angular frequencies given by $\omega=2\pi\nu$.

It should be appreciated that the prior art teaches many algorithms for use in spatially and temporally decomposing a signal from a phased array of sensors, and the present invention is not restricted to any particular algorithm. One particular adaptive array processing algorithm is the Capon method/algorithm. While the Capon method is described as one method, the present invention contemplates the use of other adaptive array processing algorithms, such as MUSIC algorithm. The present invention recognizes that such techniques can be used to determine flow rate, i.e. that the signals caused by a stochastic parameter convecting with a flow are time stationary and have a coherence length long enough that it is practical to locate sensor units apart from each other and yet still be within the coherence length. Convective characteristics or parameters have a dispersion relationship that can be approximated by the straight-line equation, $$k=\omega/u, \qquad \text{(Eqn 13)}$$

where u is the convection velocity (flow velocity). A plot of k-ω pairs is obtained from a spectral analysis of sensor samples associated with convective parameters. The pairings are portrayed so that the energy of the disturbance spectrally corresponding to the pairings can be described as a substantially straight ridge, a ridge that in turbulent boundary layer theory is called a convective ridge. What is being sensed are not discrete events of turbulent eddies, but rather a continuum of possibly overlapping events forming a temporally stationary, essentially white process over the frequency range of interest. In other words, the convective eddies 146 are distributed over a range of length scales and hence temporal frequencies.

To calculate the power in the k-ω plane, as represented by a k-ω plot (see FIG. 8) of either one of the signals, the array processor 156 determines the wavelength and so the (spatial) wavenumber k, and also the (temporal) frequency and so the angular frequency ω, of various of the spectral components of the stochastic parameter. There are numerous algorithms available in the public domain to perform the spatial/temporal decomposition of arrays of sensors 118. The present invention may use temporal and spatial filtering to precondition the signals to effectively filter out the common mode characteristics $P_{common\ mode}$ and other long wavelength (compared to the sensor spacing) characteristics in the pipe 124 by differencing adjacent sensors 118 and retaining a substantial portion of the stochastic parameter associated with the flow field and any other short wavelength (compared to the sensor spacing) low frequency stochastic parameters. In the case of suitable turbulent eddies 146 (see FIG. 7) being present, the power in the k-ω plane shown in the k-ω plot of FIG. 8 shows a convective ridge 154. The convective ridge 154 represents the concentration of a stochastic parameter that convects with the flow and is a mathematical manifestation of the relationship between the spatial variations and temporal variations described above. Such a plot will indicate a tendency for k-ω pairs to appear more or less along a line 154 with some slope, the slope indicating the flow velocity.

Once the power in the k-ω plane is determined, a convective ridge identifier 158 uses one or another feature extraction method to determine the location and orientation (slope) of any convective ridge 154 present in the k-ω plane. In one embodiment, a so-called slant stacking method is used, a method in which the accumulated frequency of k-ω pairs in the k-ω plot along different rays emanating from the origin are compared, each different ray being associated with a different trial convection velocity (in that the slope of a ray is assumed to be the flow velocity or correlated to the flow velocity in a known way). The convective ridge identifier 158 provides information about the different trial convection velocities, information referred to generally as convective ridge information to an analyzer 160. The analyzer 160 then examines the convective ridge information including the convective ridge orientation (slope). Assuming the straight-line dispersion relation given by $k=\omega/u$, the analyzer 160 determines the flow velocity, Mach number and/or volumetric flow, which are output as signals 138. The volumetric flow is determined by multiplying the cross-sectional area of the inside of the pipe 124 with the velocity of the process flow.

Speed of Sound (SOS)

Figure 9:
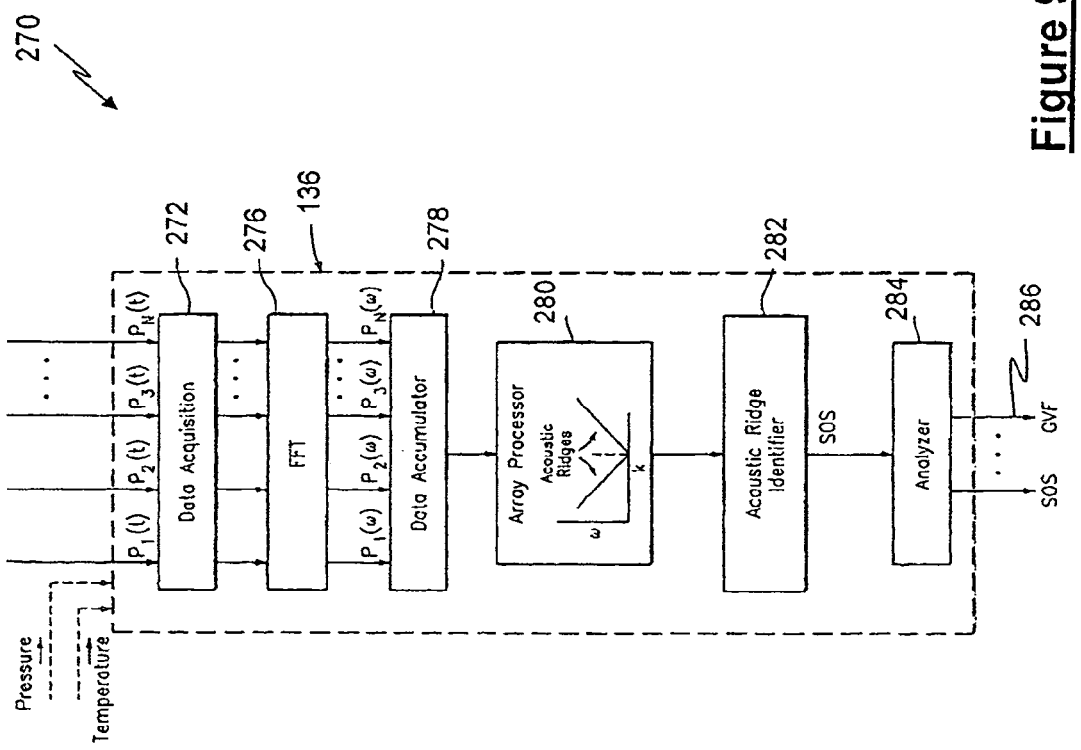
FIG. 9 is a block diagram of a second embodiment of a flow logic used in the apparatus of the present invention.

As shown in FIG. 9, the SOS Logic 270 includes a data acquisition unit 272 that digitizes the pressure signals $P_1(t)$-$P_N(t)$ associated with the acoustic waves 274 propagating through the pipe 124. Similarly to the FFT logic 150 in FIG. 7, an FFT logic 276 calculates the Fourier transform of the digitized time-based input signals $P_1(t)$-$P_N(t)$ and provides complex frequency domain (or frequency based) signals $P_1(\omega),P_2(\omega),P_3(\omega),P_N(\omega)$ indicative of the frequency content of the input signals. A data accumulator 278 accumulates the signals $P_1(t)$-$P_N(t)$ from the sensors, and provides the data accumulated over a sampling interval to an array processor 280, which performs a spatial-temporal (two-dimensional) transform of the sensor data, from the x-t domain to the k-$\omega$ domain, and then calculates the power in the k-$\omega$ plane, as represented by a k-$\omega$ plot, similar to that provided by the convective array processor 156. To calculate the power in the k-$\omega$ plane, as represented by a k-$\omega$ plot (see FIG. 10) of either the signals or the differenced signals, the array processor 280 determines the wavelength and so the (spatial) wavenumber k, and also the (temporal) frequency and so the angular frequency $\omega$, of various of the spectral components of the stochastic parameter. There are numerous algorithms available in the public domain to perform the spatial/temporal decomposition of the array of pressure sensors 118.

Figure 10:
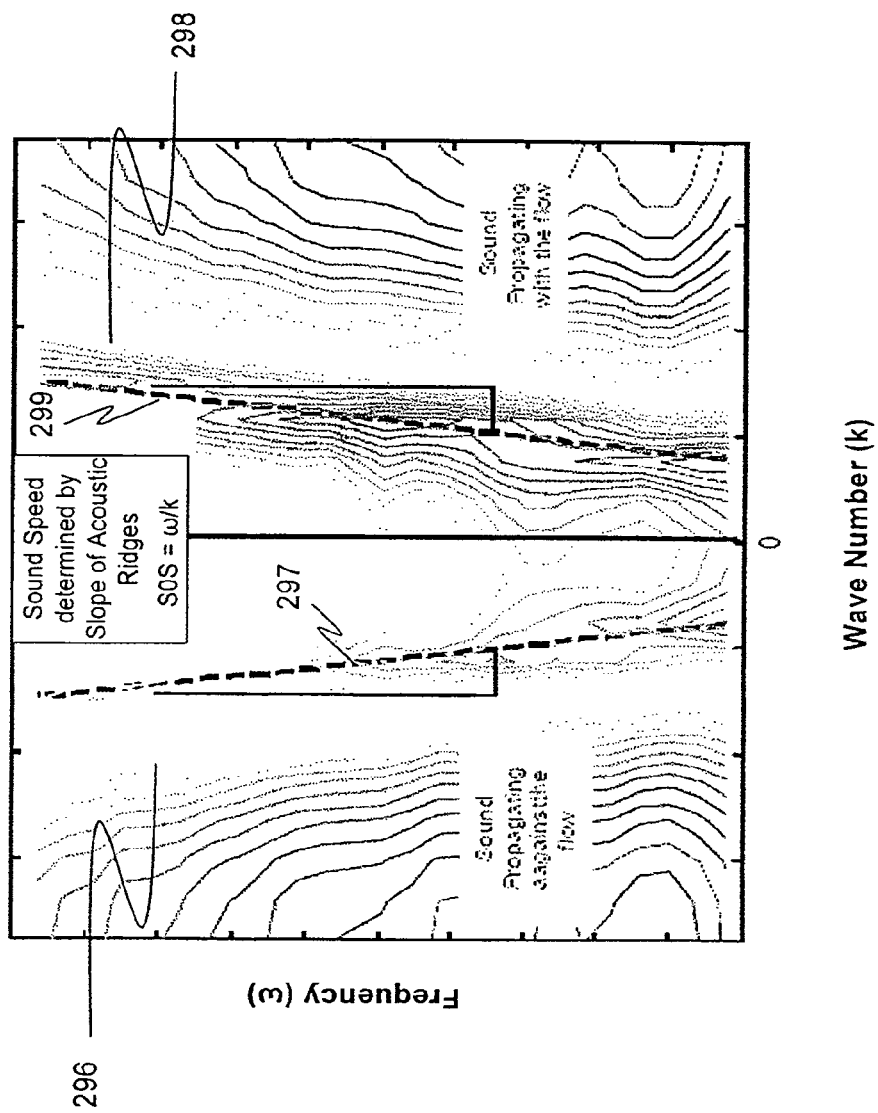
FIG. 10 a k-ω plot of data processed from an apparatus embodying the present invention that illustrates slope of the acoustic ridges.

In the case of suitable acoustic waves 274 being present in both axial directions, the power in the k-$\omega$ plane shown in a k-$\omega$ plot of FIG. 10 so determined will exhibit a structure that is called an acoustic ridge 296, 298 in both the left and right planes of the plot, wherein one of the acoustic ridges 296 is indicative of the speed of sound traveling in one axial direction and the other acoustic ridge 298 being indicative of the speed of sound traveling in the other axial direction. The acoustic ridges 296, 298 represent the concentration of a stochastic parameter that propagates through the flow and is a mathematical manifestation of the relationship between the spatial variations and temporal variations described above. Such a plot will indicate a tendency for k-$\omega$ pairs to appear more or less along a line 297, 299 with some slope, the slope indicating the speed of sound. The power in the k-$\omega$ plane so determined is then provided to an acoustic ridge identifier 282, which uses one or another feature extraction method to determine the location and orientation (slope) of any acoustic ridge present in the left and right k-$\omega$ plane. The velocity may be determined by using the slope of one of the two acoustic ridges 296, 298 or averaging the slopes of the acoustic ridges 296, 298.

Finally, information including the acoustic ridge orientation (slope) is used by an analyzer 284 to determine the flow parameters 286 relating to measured speed of sound, such as the consistency or composition of the flow, the density of the flow, the average size of particles in the flow, the air/mass ratio of the flow, gas volume fraction of the flow, the speed of sound propagating through the flow, and/or the percentage of entrained air within the flow.

Similar to the array processor 156, the array processor 280 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$ where $\lambda$ is the wavelength of a spectral component, and corresponding angular frequencies given by $\omega=2\pi\nu$.

One such technique of determining the speed of sound propagating through the fluid stream 104 is by using array processing techniques to define an acoustic ridge in the k-$\omega$ plane as shown in FIG. 10. The slope of the acoustic ridge is indicative of the speed of sound propagating through the fluid stream 104. The speed of sound (SOS) is determined by applying sonar arraying processing techniques to determine the speed at which the one dimensional acoustic waves propagate past the axial array of unsteady pressure measurements distributed along the pipe 124.

The sonar flow meter 116 of the present invention measures the speed of sound (SOS) of one-dimensional sound waves propagating through the mixture to determine the gas volume fraction of the mixture. It is known that sound propagates through various mediums at various speeds in such fields as SONAR and RADAR fields. The speed of sound propagating through the pipe 124 and fluid stream 104 may be determined using a number of known techniques, such as those set forth in U.S. patent application Ser. No. 09/344,094, filed Jun. 25, 1999, now U.S. Pat. No. 6,354,147; U.S. patent application Ser. No. 10/795,111, filed Mar. 4, 2004; U.S. patent application Ser. No. 09/997,221, filed Nov. 28, 2001, now U.S. Pat. No. 6,587,798; U.S. patent application Ser. No. 10/007,749, filed Nov. 7, 2001, and U.S. patent application Ser. No. 10/762,410, filed Jan. 21, 2004, each of which are incorporated herein by reference.

While a sonar-based flow meter using an array of sensors 118 to measure the speed of sound of an acoustic wave propagating through the mixture 104 is shown and described, one will appreciate that any means for measuring the speed of sound of the acoustic wave may used to determine the entrained gas volume fraction of the mixture/fluid or other characteristics of the flow described hereinbefore.

The GVF meter may employ any technique that measures the sound speed of a fluid. However, it is particularly synergistic with meters such as described in U.S. Pat. No. 6,889,562, and U.S. Pat. No. 6,609,609, which are incorporated herein by reference, in that the sound speed measurement, and thus gas volume fraction measurement, can be accomplished using the same hardware as that used for volumetric flow measurement. It should be noted, however, that the gas volume fraction measurement could be performed independently of a volumetric flow measurement, and would have utility as an important process measurement in isolation or in conjunction with other process measurements. U.S. Patent Application Publication No. 2004/0255695 published Dec. 23, 2004, U.S. Patent Application Publication No. 2005/0044929 published Mar. 3, 2005, and U.S. Patent Application Publication No. 2005/0061060 published Mar. 24, 2005, which are all incorporated by reference herein, also describe examples of such meters.

A pressure sensor and/or temperature sensor measures the pressure and/or temperature of the liquid. Alternatively, the pressure and/or temperature may be estimated rather than actually measured. In response to the measured speed of sound, and the pressure and temperature, the signal processor determines the GVF of the liquid.

Figure 11:
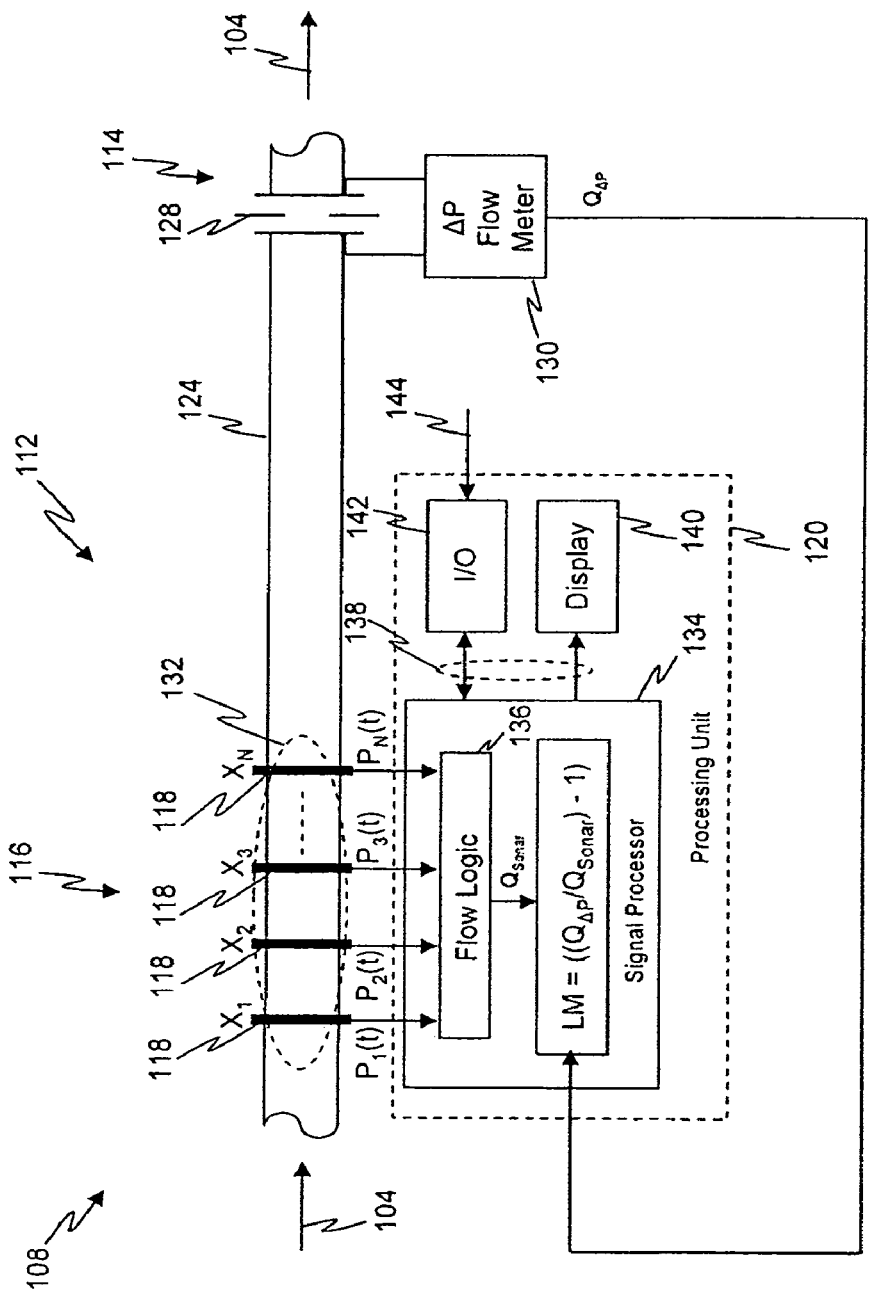
FIG. 11 is general overall schematic diagram illustrating another embodiment of an apparatus for measuring wetness and volumetric flow rate of a gas flow within a pipe, wherein the sonar meter is disposed upstream of the DP meter in accordance with the present invention.

Referring to FIG. 11, a schematic diagram of an additional embodiment of an apparatus 112 for measuring wetness and volumetric flow rate of a gas flow 104 within a pipe 124 is shown, wherein the sonar meter 116 is disposed upstream of the DP meter 114 in accordance with the present invention. The sonar meter 116 placed upstream of the DP meter 114 advantageously provides a well mixed liquid gas flow 104 to be measured by the sonar meter 116. It should be appreciated that some or all of the functions within the flow logic 136 may be implemented in software (using a microprocessor or computer) and/or firmware, or may be implemented using analog and/or digital hardware, having sufficient memory, interfaces, and capacity to perform the functions described herein.

As suggested hereinbefore, the sonar flow meter 116 may comprise a plurality of ultrasonic sensors 118 to provide an output signal $P_N(t)$, for example a velocity measurement. The ultrasonic sonar flow meter 116 is similar to that described in U.S. patent application Ser. No. 10/756,977 filed on Jan. 13, 2004 and U.S. patent application Ser. No. 10/964,043 filed on Oct. 12, 2004, which are incorporated herein by reference. Furthermore, it should be appreciated that the sonar meter 116 may be substituted with an ultrasonic sensor meter that uses any one of the following types of meters: Transit Time Ultrasonic Flow Meter (TTUF), Doppler Ultrasonic Flowmeter (DUF), and Cross Correlation Ultrasonic Flow Meter (CCUF), similar to that described in the article "Guidelines for the Use of Ultrasonic Non-Invasive Metering Techniques" by M. L. Sanderson and H. Yeung, published on Jul. 17, 2002, which is incorporated herein by reference. One such CCUF is the GE Panametrics DigitalFlow™ CTF878 flowmeter having a pair of ultrasonic sensors disposed axially along the pipe 108, which is incorporated herein by reference.

While the meters 116 (e.g., sonar meter and ultrasonic meter) combined with the differential meter 114 include a sonar meter or an ultrasonic meter, the present invention contemplates that such meters may be any meter that provides an output measurement that provides a repeatable over report function (or output signal) with respect to the wetness of the flow, wherein the over reporting is substantially less than the over reporting of the DP meter 114. The greater the difference in the over reporting between the meter 116 and the DP meter 114, the greater the accuracy and resolution of the wetness measurement.

Figure 12:
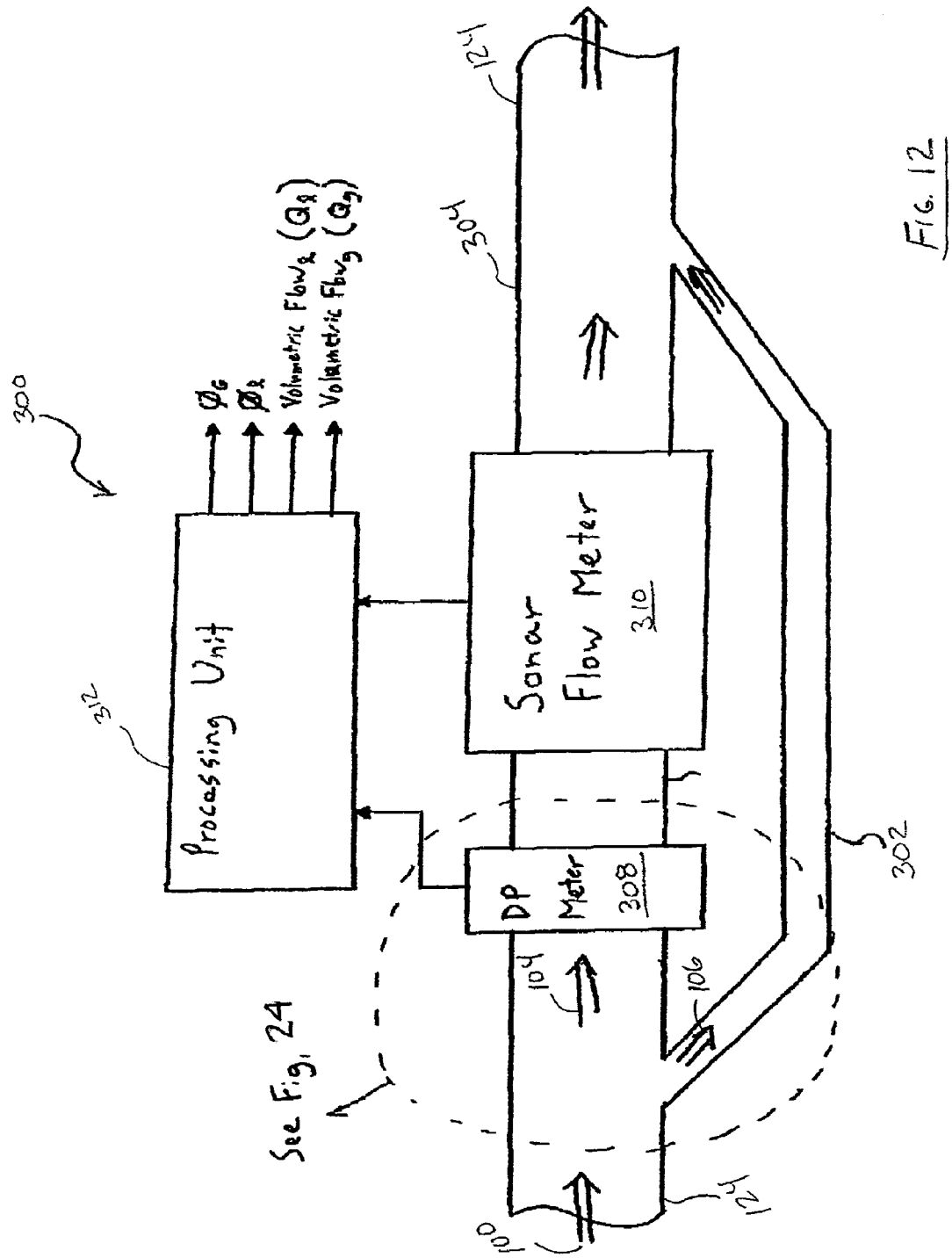
FIG. 12 illustrates a flow meter system having a bypass pipe to separate the fluid flow and measure parameters of a fluid flow including a multiphase fluid flow, in accordance with the present invention.

Referring to FIG. 12, a first embodiment of the multiphase meter 300 having a separator portion 102 in accordance with the present invention is illustrated for providing outputs that include the phase fraction of each of the phases of the fluid flow 100 and the volumetric flow rate of each of the phases. The phase of the fluid 100 may comprise a gas-liquid mixture or a liquid-liquid-gas mixture (such as oil, gas and water) in the form of a wet gas mixture. The flow meter 300 includes a bypass pipe 302 for separating the wet gas mixture into a liquid flow 106 and a gas flow 104, wherein the liquid portion 106 of the mixture 100 flows through the bypass pipe 302 and the gas portion 104 of the mixture 100 (which may include some liquid droplets or mist) flows through a primary pipe 304. It should be appreciated that the bypass pipe 302 may include a smaller cross-sectional area than the primary pipe 304 in order to accommodate the lesser amount of liquid in the flow 100. Similar to that described hereinbefore, the flow meter 302 may include a DP meter 308 and a sonar flow meter 310 to provide a volumetric flow rate and phase fraction for each of the phases passing through the primary pipe 304, as described hereinbefore. A processor 312 further adds to these outputs the amount of liquid flowing through the bypass pipe 302. Assuming the fluid flowing through the bypass pipe 302 is all liquid, and knowing that the differential pressure across the bypass pipe 302 is the same as the differential of the DP meter 308, the flow rate and hence the volumetric flow rate can be determined.

Figure 13:
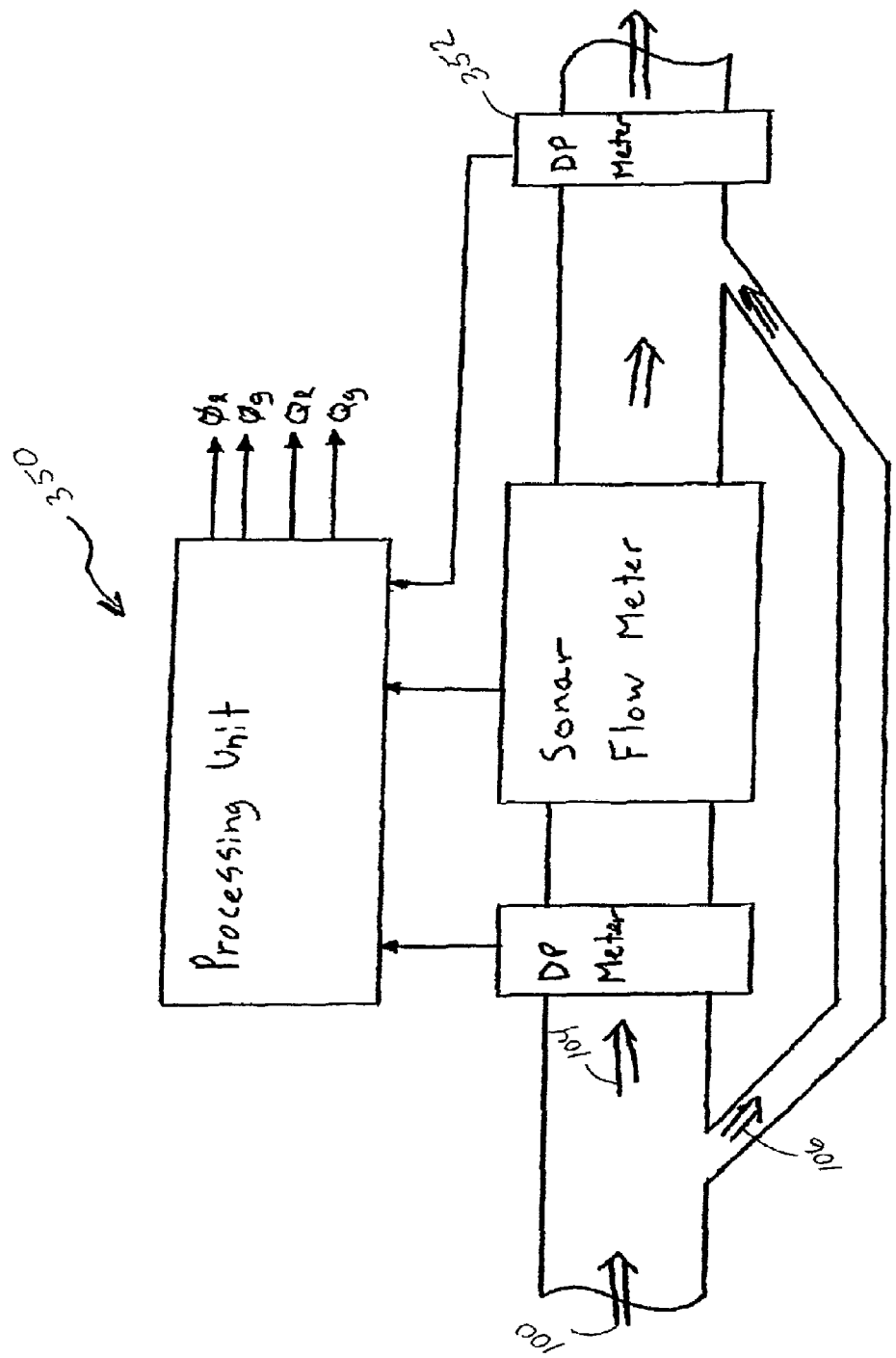
FIG. 13 illustrates a flow meter system having a bypass pipe to separate the fluid flow and measure parameters of a fluid flow including a multiphase fluid flow, in accordance with the present invention.
Figure 14:
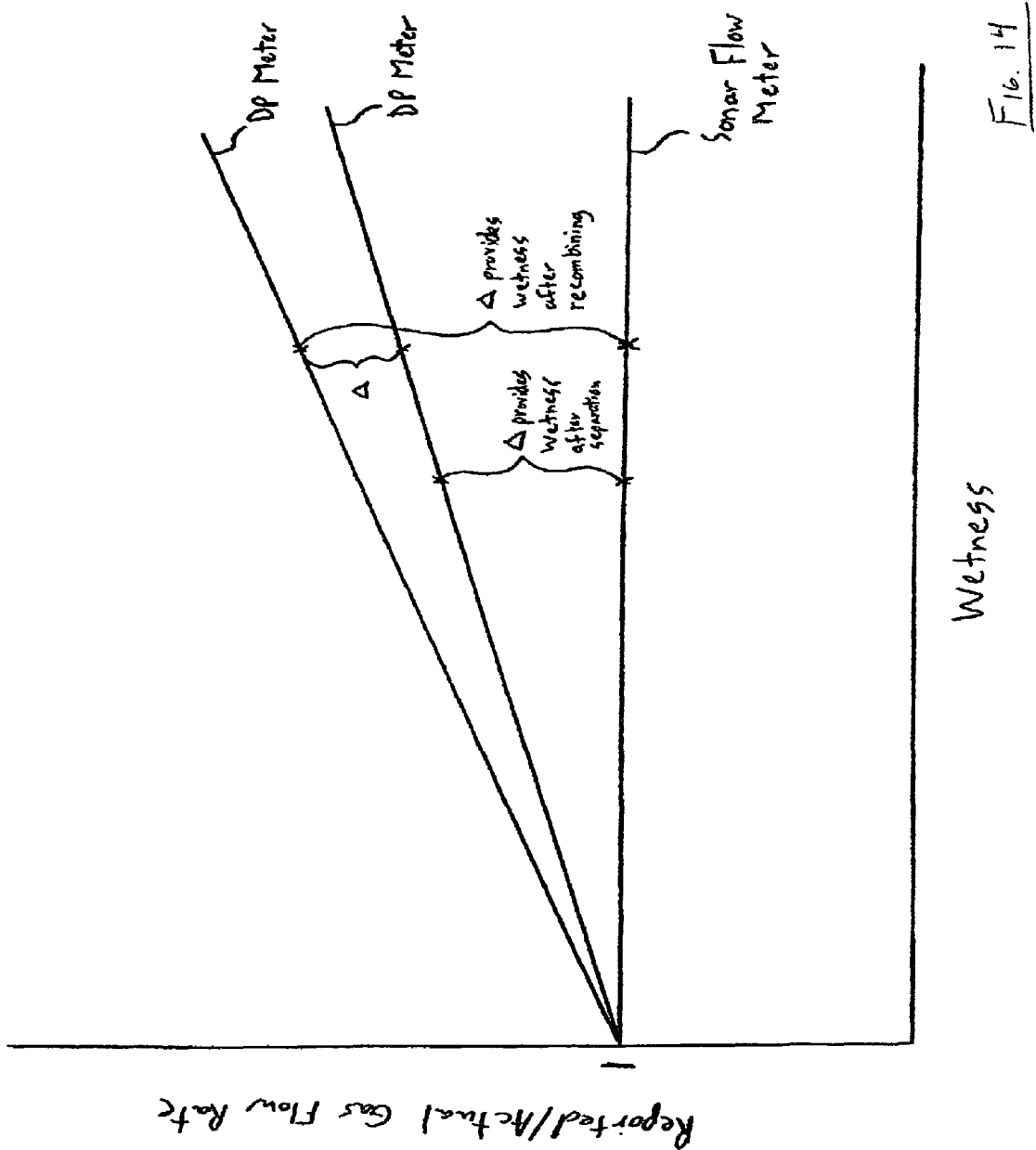
FIG. 14 shows a plot illustrating the relationship between actual/reported gas flow rates and wetness, in accordance with the present invention.

Referring to FIG. 13, a second embodiment of a flow meter 350 is shown and is similar to that illustrated in FIG. 12, with the exception that a second DP meter 352 is provided after the recombination of the separated flows 104,106. The second DP meter 352 may be similar to the DP meter 308 on the primary pipe 304, such as an orifice plate, cone meter (e.g., venturi), or similar device to provide a pressure difference across the device. Alternatively, the DP meter 352 may be different which will provide additional information to characterize and measure the flow 100. The second or added DP meter 352 may provide a means to measure and characterize the flow 106 passing through the bypass pipe 302. As shown in FIG. 14, the wetness of the fluid can be measured in the primary pipe 304 and the output pipe 124 after the flows 104,106 are recombined. This difference in wetness at these locations enables measurement of the phase fraction of the fluid flow 100.

Figure 15:
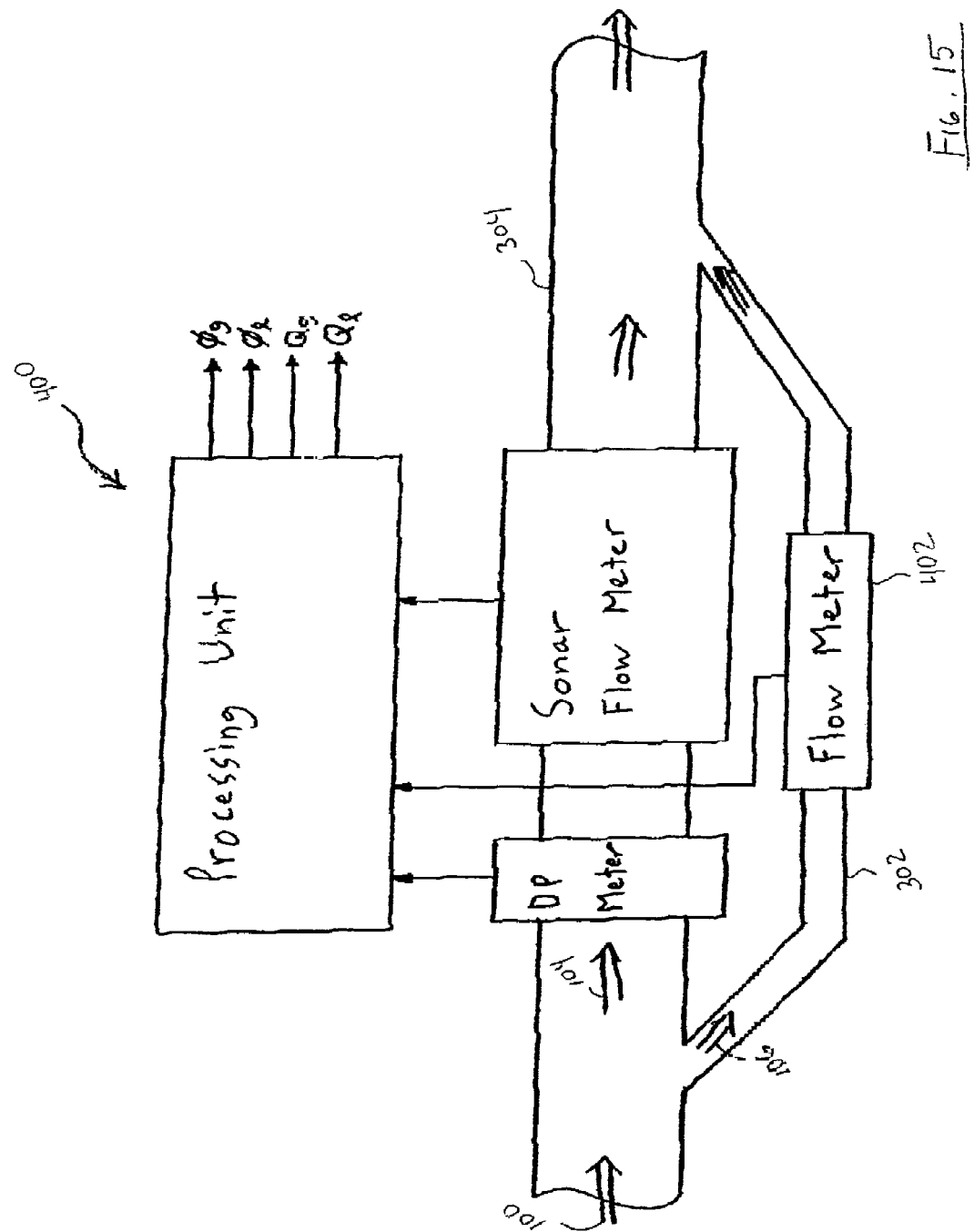
FIG. 15 illustrates a flow meter system having a bypass pipe to separate the fluid flow and measure parameters of a fluid flow including a multiphase fluid flow, in accordance with the present invention.

Referring to FIG. 15, a third embodiment of a flow meter 400 is illustrated, wherein the flow meter 400 includes a flow meter 402 disposed to directly measure the flow rate of the liquid flowing within the bypass pipe 302. The flow meter 402 may be any flow meter known in the art. The flow meter 400 provides for a more direct measurement of the flow 106 through the bypass pipe 302.

Figure 16:
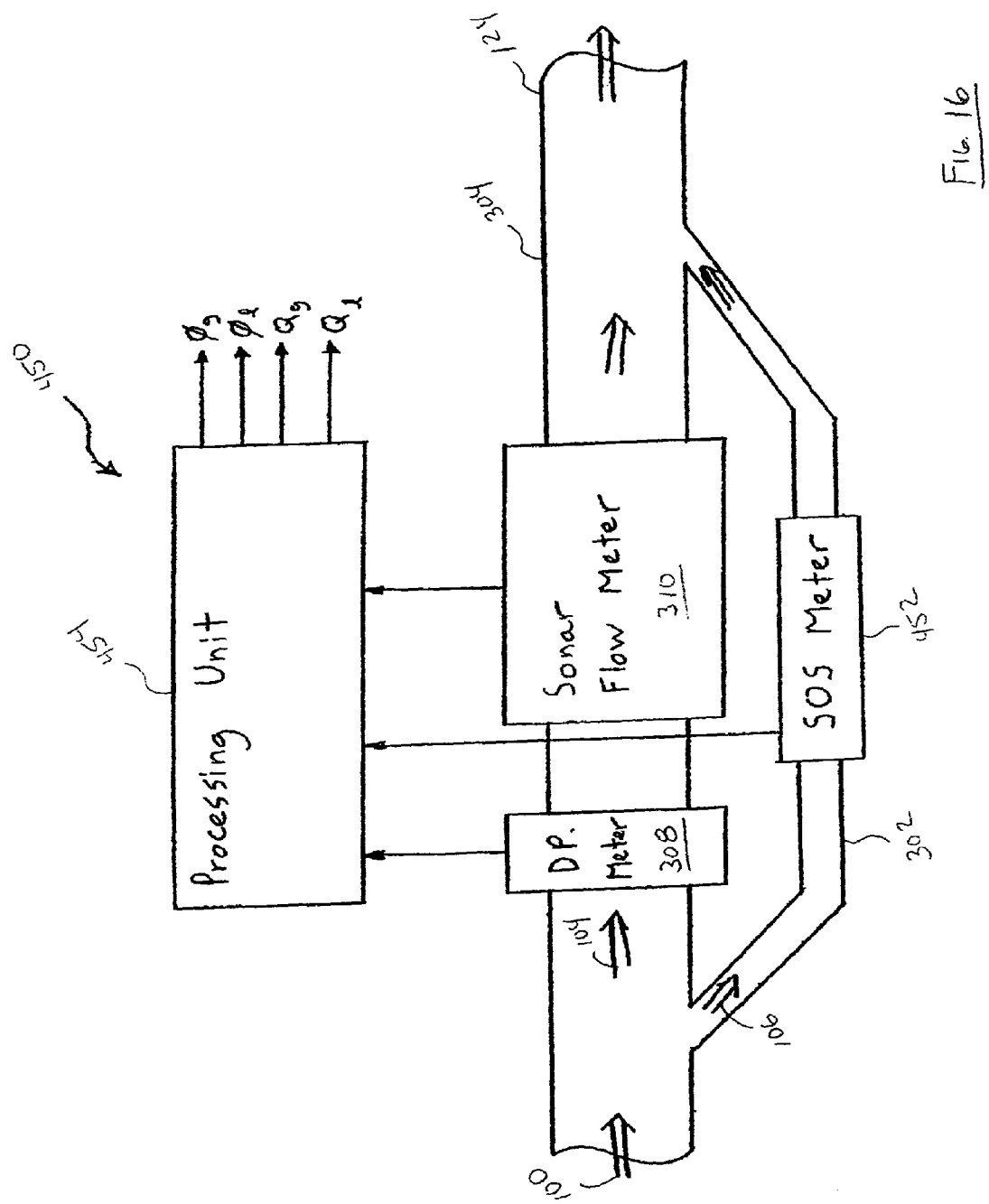
FIG. 16 illustrates a flow meter system having a bypass pipe to separate the fluid flow and measure parameters of a fluid flow including a multiphase fluid flow, in accordance with the present invention.

Referring to FIG. 16, a fourth embodiment of a flow meter 450 is illustrated, wherein the flow meter 450 includes an SOS meter 452 that measures the speed of sound of a one-dimensional sound wave propagating longitudinally through the bypass pipe 302. The SOS meter 450 may comprise an array of sensors disposed along the pipe 302, similar to that described in U.S. Pat. No. 6,354,147, filed on Jun. 25, 1999, U.S. Pat. No. 6,587,798, filed on Nov. 28, 2001, and U.S. patent application Ser. No. 10/762,410, filed on Jan. 21, 2004, which are incorporated herein by reference, as described hereinbefore. Knowing the speed of sound of the fluid flow 106, the composition of the fluid flowing through the bypass pipe 302 can be determined. The SOS meter 452 can determine when liquid is present. If so, the flow meter 450 knows when fluid is flowing through the bypass pipe 302 and functions or processes the data as discussed for the flow meter illustrated hereinabove. If the SOS meter 452 detects gas, the processing unit 454 can correct or adjust the output measure for air passing through the bypass pipe 302. Alternatively, the SOS meter 452 may be a combination SOS meter 452 and a flow meter similar to that described in U.S. patent application Ser. No. 10/875,857, filed on Jun. 24, 2004, which is incorporated herein by reference, to provide additional information or measurement of the fluid in the bypass pipe 302 to provide a more accurate measurement. Specifically, the combination SOS meter and flow meter comprise an array of sensors (e.g., strained-based sensors), which sensed parameters that convect with the flow and acoustic waves propagating through the flow. The pressure signals are processed by the processor in accordance with the velocity and SOS logic described herein before to provide velocity, volumetric flow rate, SOS, and gas volume fraction.

Figure 17:
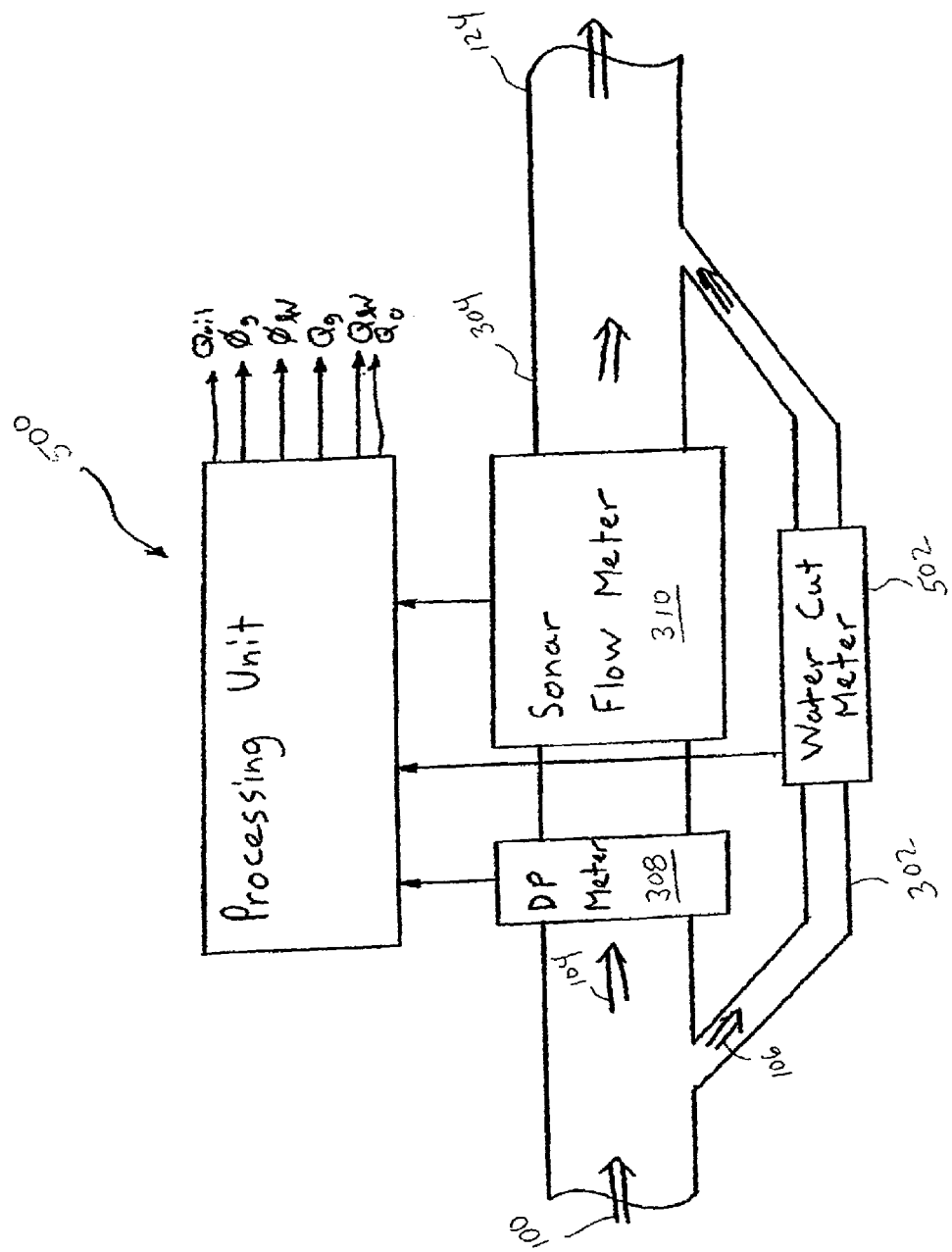
FIG. 17 illustrates a flow meter system having a bypass pipe to separate the fluid flow and measure parameters of a fluid flow including a multiphase fluid flow, in accordance with the present invention.
Figure 18:
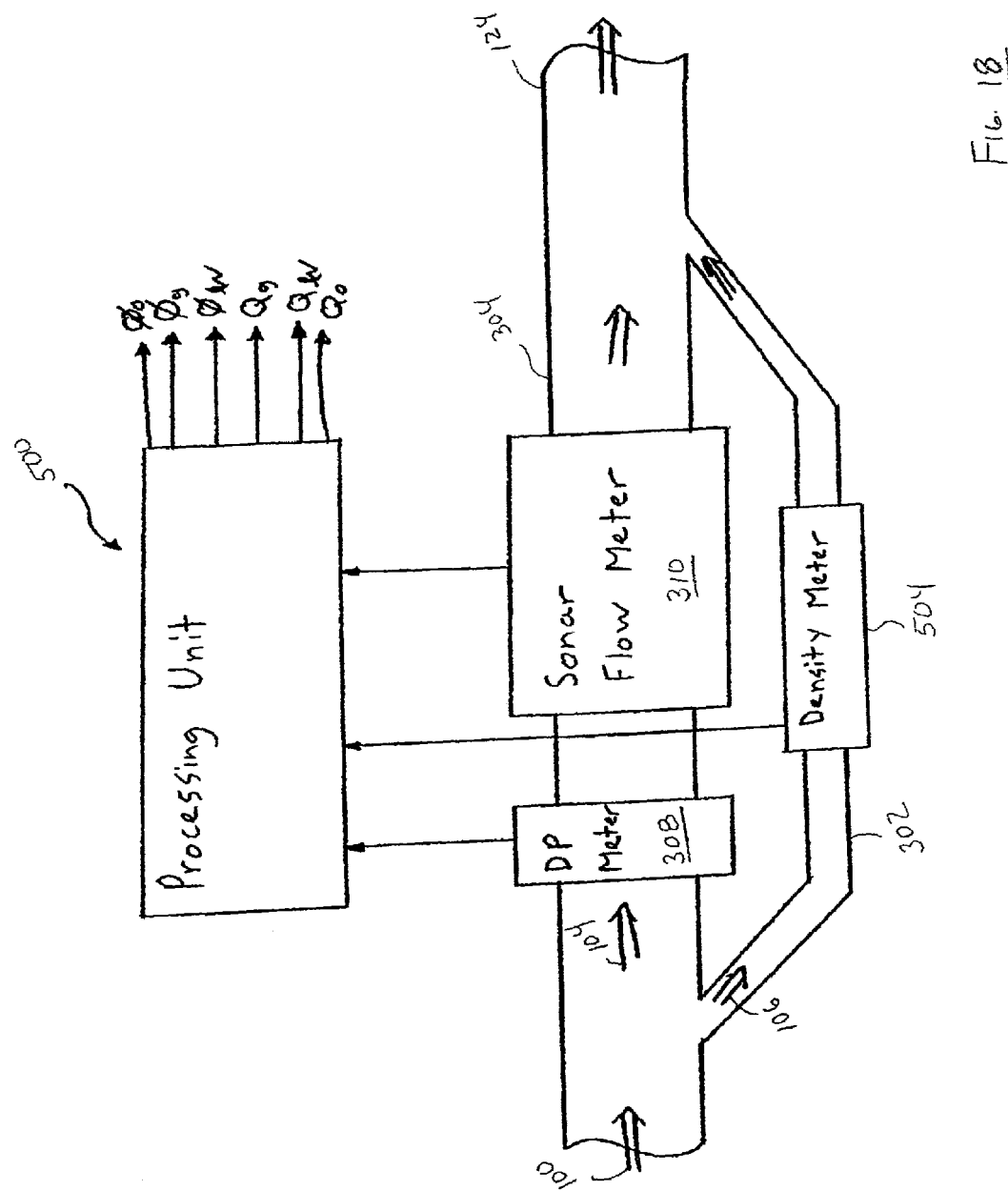
FIG. 18 illustrates a flow meter system having a bypass pipe to separate the fluid flow and measure parameters of a fluid flow including a multiphase fluid flow, in accordance with the present invention.
Figure 19:
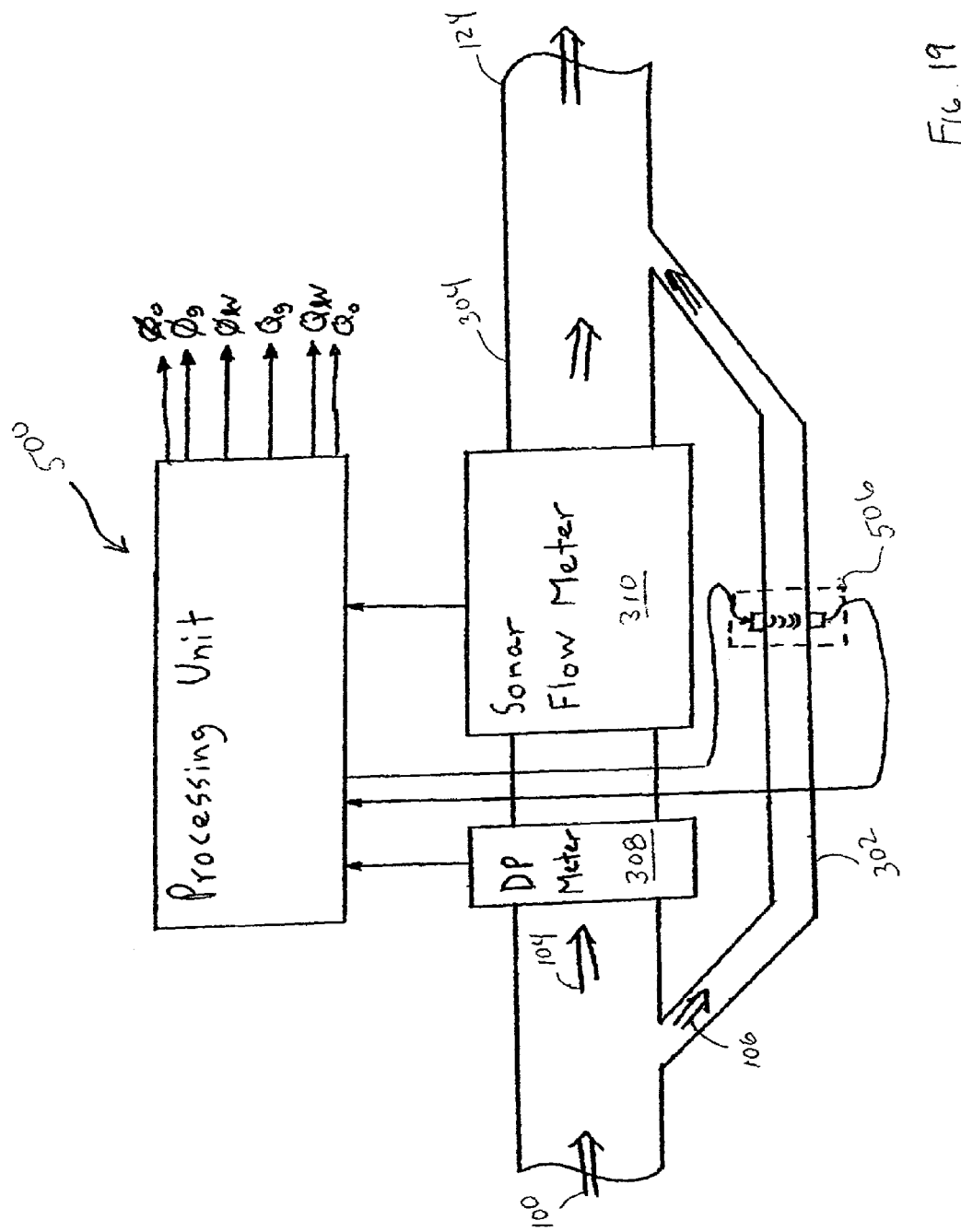
FIG. 19 illustrates a flow meter system having a bypass pipe to separate the fluid flow and measure parameters of a fluid flow including a multiphase fluid flow, in accordance with the present invention.

Referring to FIG. 17, a fifth embodiment of a flow meter 500 is illustrated, wherein the flow meter 500 can provide a multi-phase measure of a liquid-liquid-gas mixture (e.g., oil, water and gas mixture) flowing within the pipe 124. The flow meter 500 includes a water/cut meter 502 disposed on the bypass pipe 302 to determine the phase fraction of the water in the bypass pipe 302. Assuming the pipe 302 is full of liquid, the water cut meter 502 provides a phase fraction of the water and oil mixture in the bypass pipe 302. Knowing this phase fraction of the oil and water in the bypass pipe 302, the volumetric flow and phase fraction of each of the phases of the mixture 100 may be determined. FIGS. 18 and 19 illustrate specific devices that may be used to determine the watercut in the bypass pipe 302. FIG. 18 shows a density meter 504 for determining the water cut. Knowing the density of water and oil, the measured density of the oil/water mixture in the bypass pipe 302 can be used to determine the phase fraction of the oil and water, as is known in the art. FIG. 19 shows an ultrasonic sensor 506 for determining the water cut, as described in U.S. patent application Ser. No. 60/758,242, filed on Jan. 10, 2006, which is incorporated herein by reference.

Specifically, the measured transit time of the ultrasonic signal is indicative of the speed of sound of the liquid. The frequency of the ultrasonic signal propagating through the fluid is greater that the bubble resonant frequency such that entrained gas goes not affect the ultrasonic signal. Knowing the SOS of the liquid portion of the fluid flow, the phase fraction of the water can be determined. The phase fraction of the water is a function of the SOS of the liquid, the SOS of the oil, SOS of the water, the density of the oil, and the density of the water. Knowing the SOS and density of the oil and water, the relationship between the phase fraction (e.g., watercut) of the flow 12 and the SOS of the liquid is known. This relationship can be illustrated in the plot of SOS of the liquid v. watercut, and therefore, knowing the SOS of the liquid, the watercut may be determined.

While each of the ultrasonic sensor 506 of FIG. 19 comprises a pair of ultrasonic sensors (transmitter and receiver) diametrically-opposed to provide through transmission, the present invention contemplates that one of the ultrasonic sensors may be offset axially such that the ultrasonic signal from the transmitter sensor has an axial component in its propagation direction.

The present invention also contemplates the ultrasonic sensor 506 may be configured in a pulse/echo configuration. In this embodiment, the ultrasonic sensor comprises one ultrasonic sensor that transmits an ultrasonic signal through the pipe wall and fluid substantially orthogonal to the direction of flow and receives a reflection of the ultrasonic signal reflected back from the wall of the pipe to the ultrasonic sensor.

Figure 20:
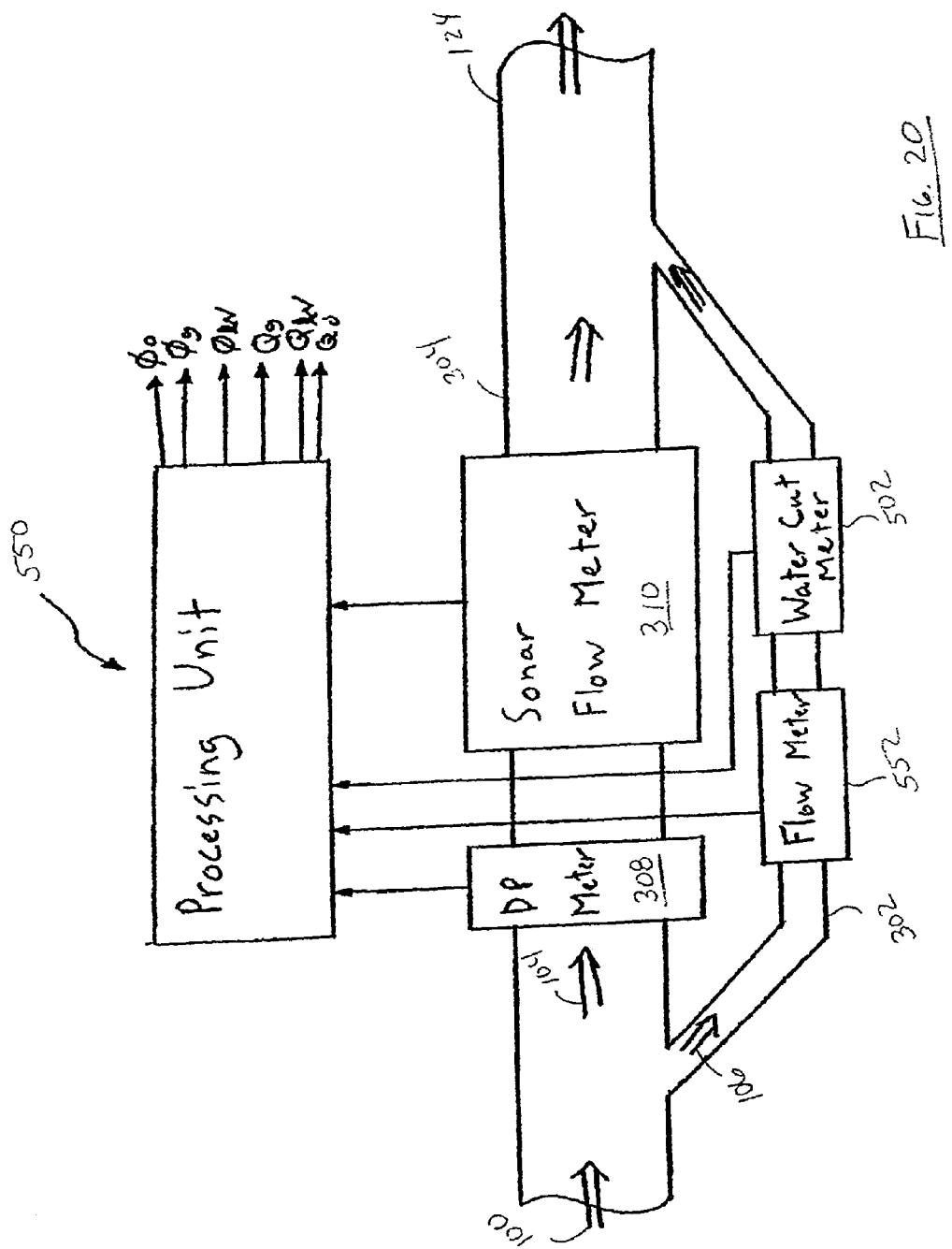
FIG. 20 illustrates a flow meter system having a bypass pipe to separate the fluid flow and measure parameters of a fluid flow including a multiphase fluid flow, in accordance with the present invention.

Referring to FIG. 20, a sixth embodiment of a multiphase flow meter 550 is illustrated and is similar to the flow meter 500 of FIG. 17, with the addition of a flow meter 552 disposed to measure the flow rate of the fluid flowing in the bypass pipe 302. This direct measurement provides a more accurate measurement of the bypass fluid than determining the flow rate based on the differential pressure across the pipe, as described hereinbefore. The flow meter 552 and water cut meter 502 may be combined into a single unit as shown and described in U.S. Patent Application No. 60/758,242, filed on Jan. 10, 2006, which is incorporated herein by reference.

Figure 21:
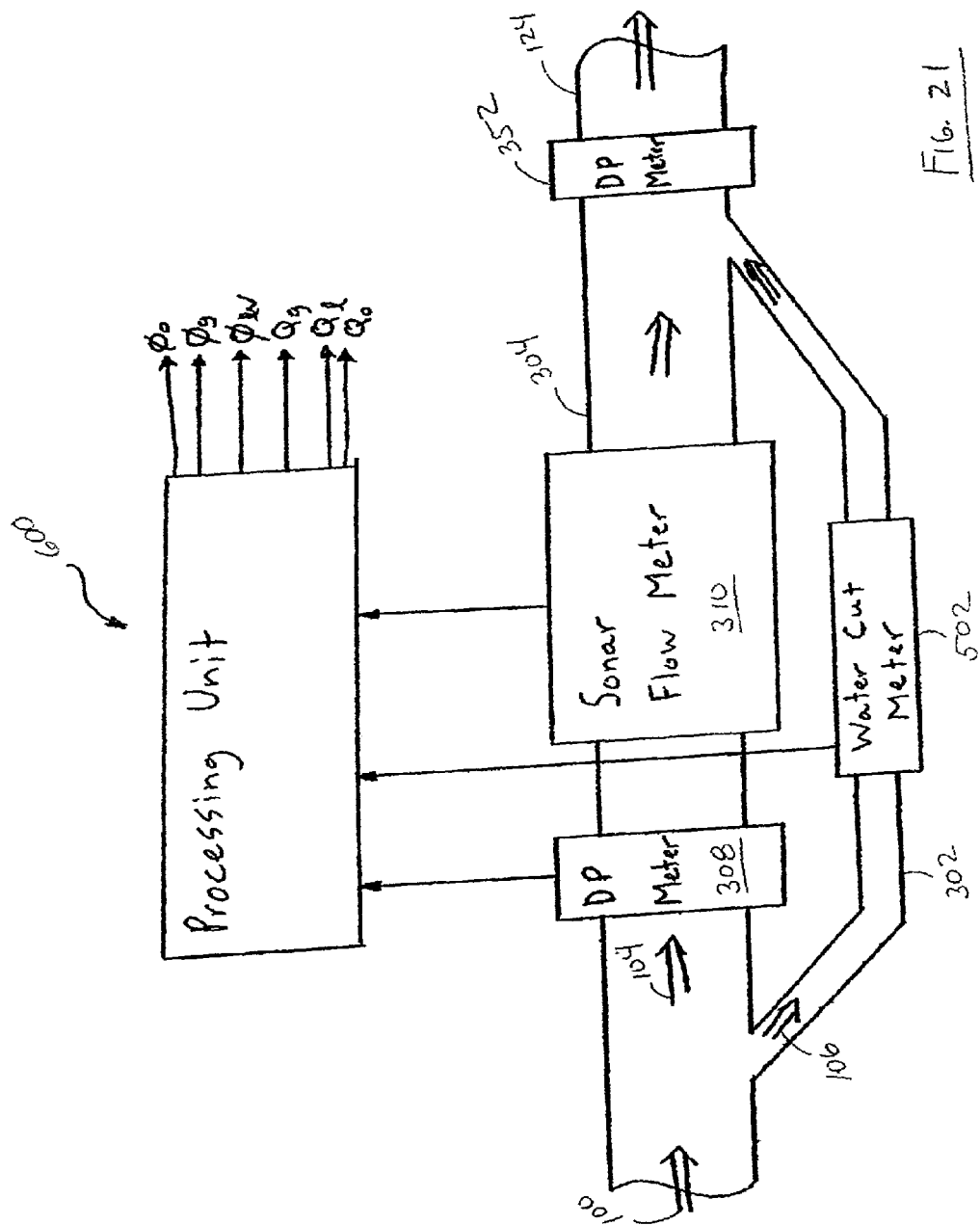
FIG. 21 illustrates a flow meter system having a bypass pipe to separate the fluid flow and measure parameters of a fluid flow including a multiphase fluid flow, in accordance with the present invention.

FIG. 21 illustrates a flow meter 600 that combines the features of the flow meter 350 of FIG. 13 and the features of the flow meter 500 of FIG. 17.

Figure 22:
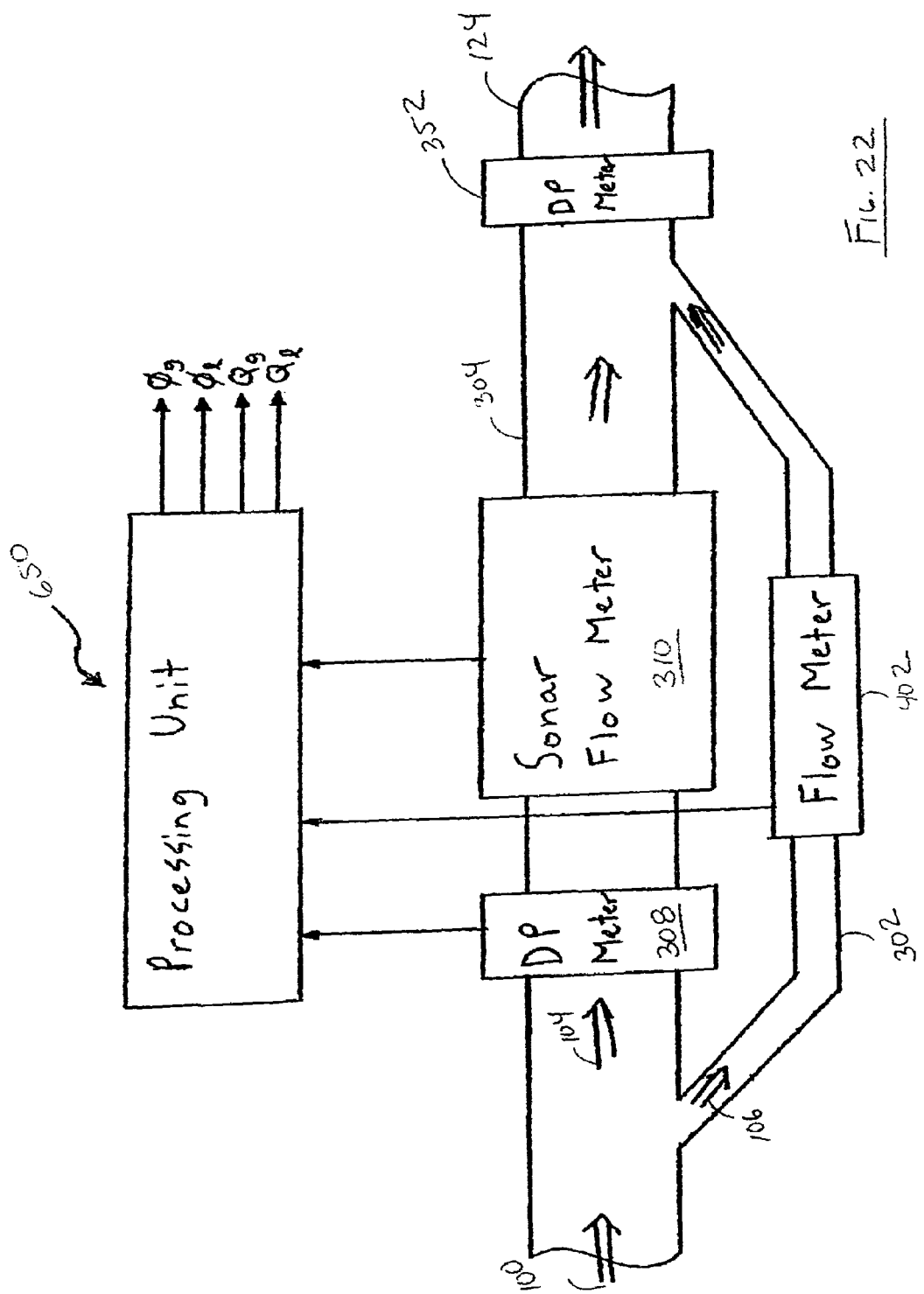
FIG. 22 illustrates a flow meter system having a bypass pipe to separate the fluid flow and measure parameters of a fluid flow including a multiphase fluid flow, in accordance with the present invention.

FIG. 22 illustrates a flow meter 650 that combines the features of the flow meter 350 of FIG. 13 and the features of the flow meter 402 of FIG. 15.

Figure 23:
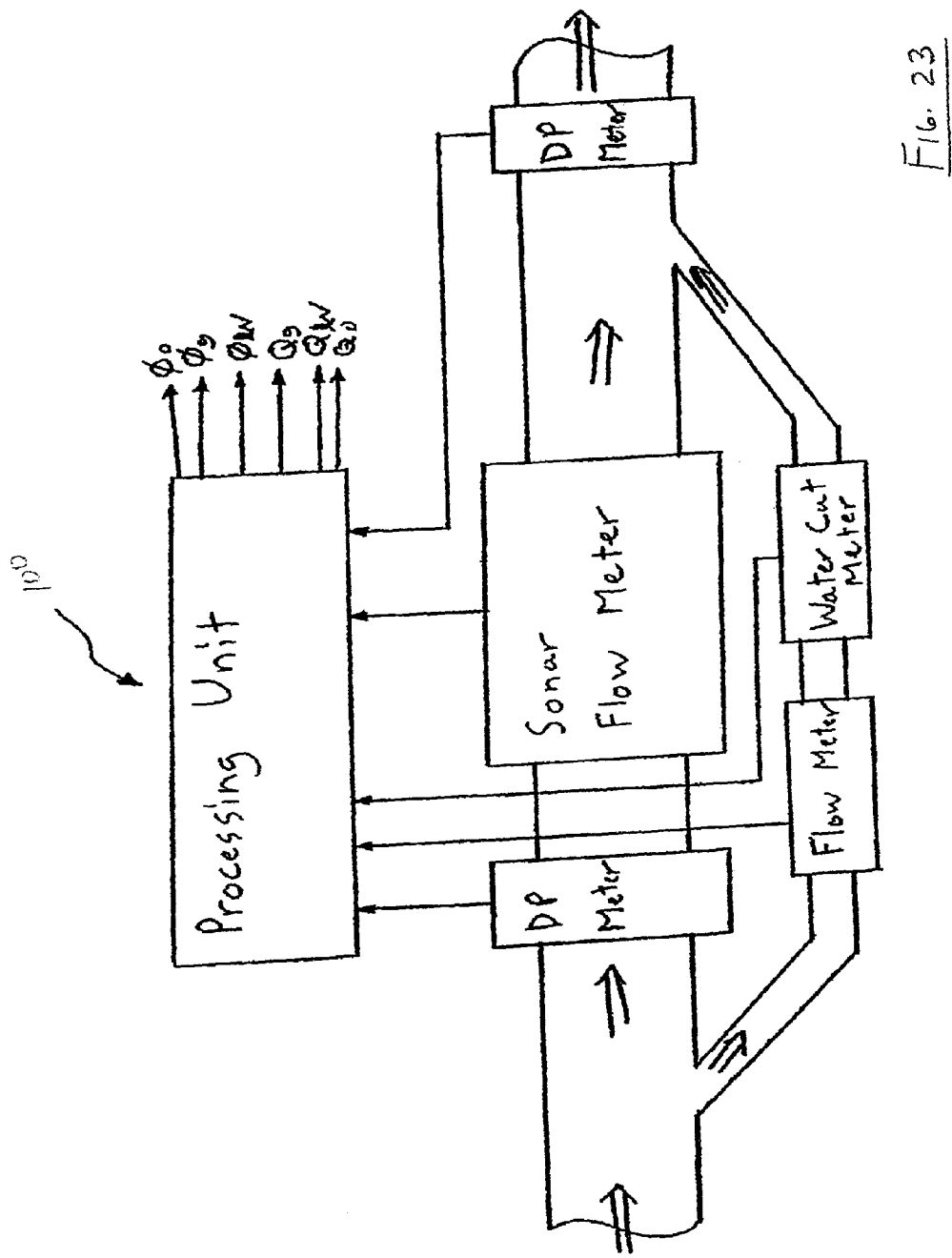
FIG. 23 illustrates a flow meter system having a bypass pipe to separate the fluid flow and measure parameters of a fluid flow including a multiphase fluid flow, in accordance with the present invention.

FIG. 23 illustrates a flow meter 700 that combines the features of the flow meter 350 of FIG. 13 and the features of the flow meter 550 of FIG. 20.

Figure 24:
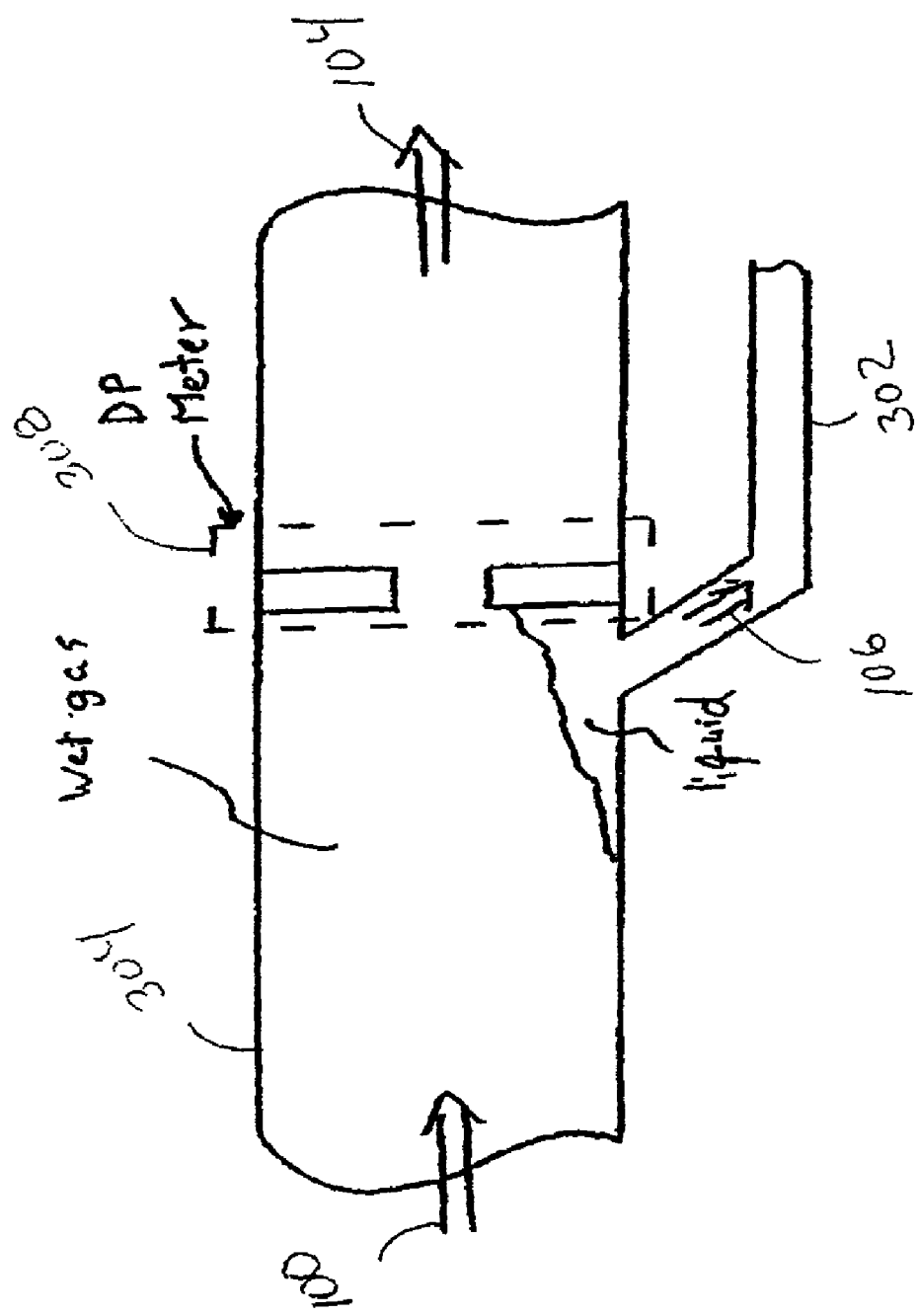
FIG. 24 illustrates a flow meter system having a bypass pipe to separate the fluid flow and measure parameters of a fluid flow including a multiphase fluid flow, in accordance with the present invention.

FIG. 24 illustrates an expanded view of the junction of the bypass pipe 302 and the DP meter 308 on the primary pipe 304. As shown the junction of the primary pipe 304 and bypass pipe 302 is near the DP meter 308 (e.g., orfice plate) where fluid builds or condenses to provide efficient separation of the liquid and gas. One will appreciate that the closer the opening of the bypass pipe 302 is to the DP meter 308, the greater the separation and less likely the bypass fluid will have any gas carry under.

Figure 25:
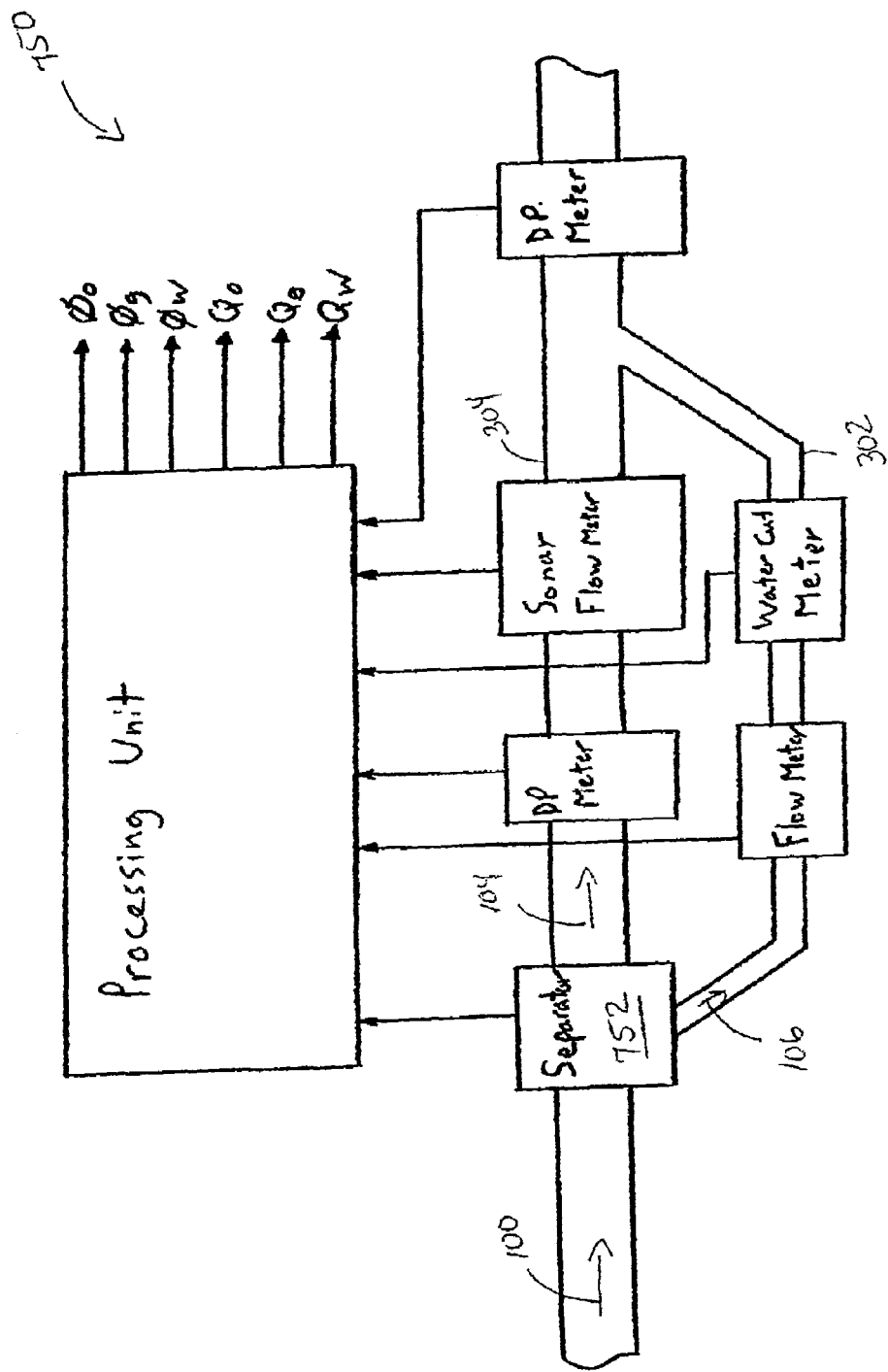
FIG. 25 illustrates a flow meter system having a bypass pipe to separate the fluid flow and measure parameters of a fluid flow including a multiphase fluid flow, in accordance with the present invention.

FIG. 25 illustrates an overall block diagram 750 of a multiphase flow measurement system similar to the system 700 as shown in FIG. 23. As shown, the system 750 includes a flow separator portion 752 that separates the wet gas flow 100 into a liquid portion 106 and a gas portion 104. The separated gas portion 104 (having some liquid carry through) passes through the primary pipe 304 and the separated liquid portion 106 (which may have some carry under gas) passes through the bypass pipe 302. The separator portion 752 may be any known means of separating gas and liquid of a multiphase flow.

Figure 26:
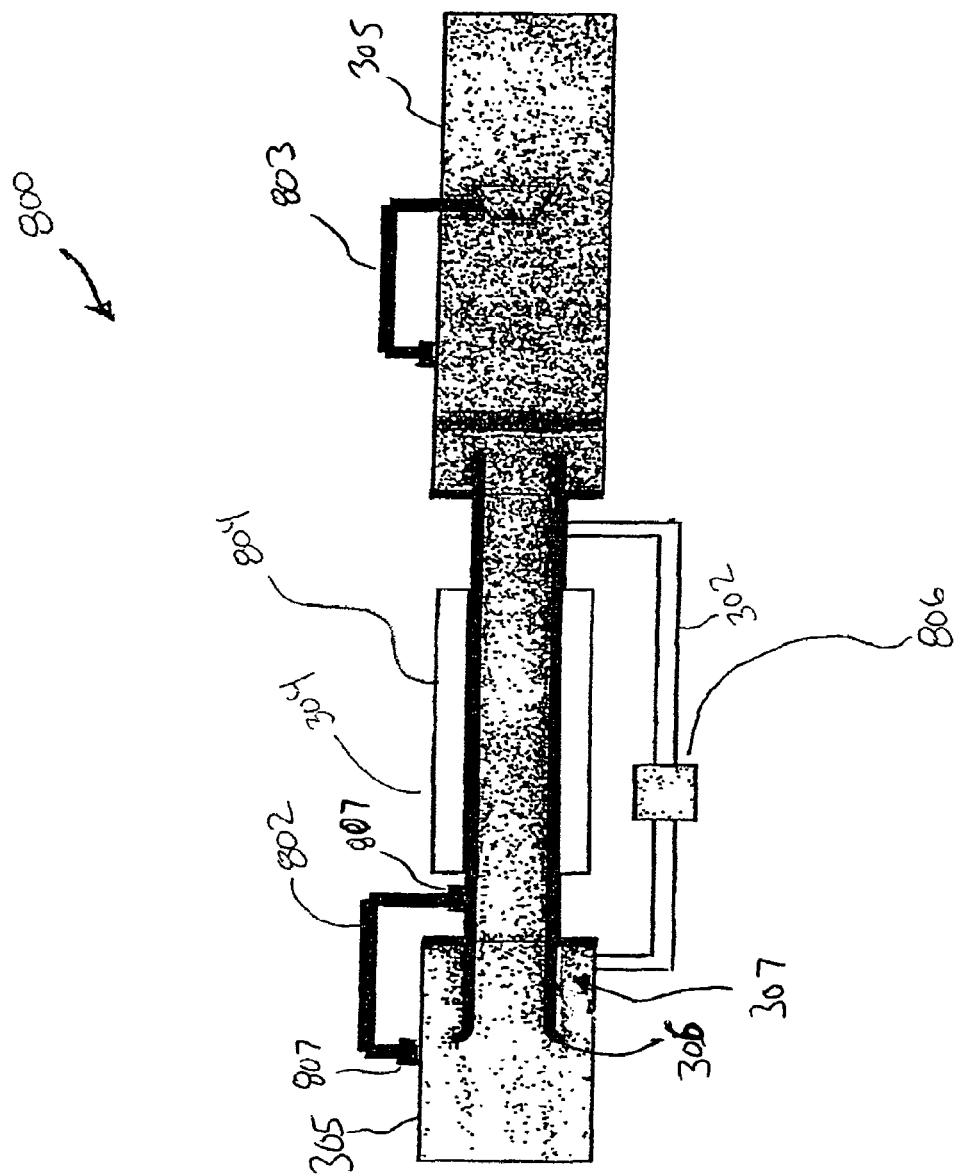
FIG. 26 illustrates a flow meter system having a bypass pipe to separate the fluid flow and measure parameters of a fluid flow including a multiphase fluid flow, in accordance with the present invention.

FIG. 26 is a seventh embodiment 800 of the sensor portion of the present invention (excluding the processing unit) similar to the system 600 shown in FIG. 21. The flow system 800 includes a pair of DP meters 802 803, a sonar flow meter 804 and a watercut meter 806. As shown, a portion of the primary pipe 304 is narrowed, wherein the sonar flow meter 804 measures a parameter of the fluid flowing through the narrowed portion. Extending from the input port (or inlet) of the narrow portion of primary pipe 304 is a flange 305 disposed circumferentially around the input port 306 for separating the liquid portion of the flow from the gas portion of the flow. The flange and narrowing portion of the primary pipe 304 provides a separator portion 307 whereby the liquid, which typically propagates along the walls of the pipe, is trapped by the flange 305 and directed into the bypass pipe 302. The cross sectional area of the bypass pipe 302 is less than the cross sectional area of the primary pipe 304 to ensure that the pipe is substantially filled with liquid. The cross sectional area of the pipe is determined to ensure that the bypass pipe 302 is continually filled with liquid with minimal pass through the narrowed portion of the primary pipe 304. The cross sectional area is therefore dependent on the velocity of the fluid within the pipe and the wetness of the fluid flow. One will appreciate that the bypass pipe 302 and narrowed portion of the primary pipe 304 may have any cross sectional shape. For example, the primary and bypass pipes may have square cross sectional areas with flat surfaces to accommodate mounting of ultrasonic sensors for the watercut meter 806 and sonar flow meter 804 using these types of sensors.

The DP meter 802 comprises a pair of pressure sensors 807, wherein one sensor is disposed on the flange 305 and the other pressure sensor is disposed on the narrowed primary pipe 304 to form a DP meter 802. The other DP meter 803 disposed on the outlet flange is shown as a v-cone meter.

Figure 27:
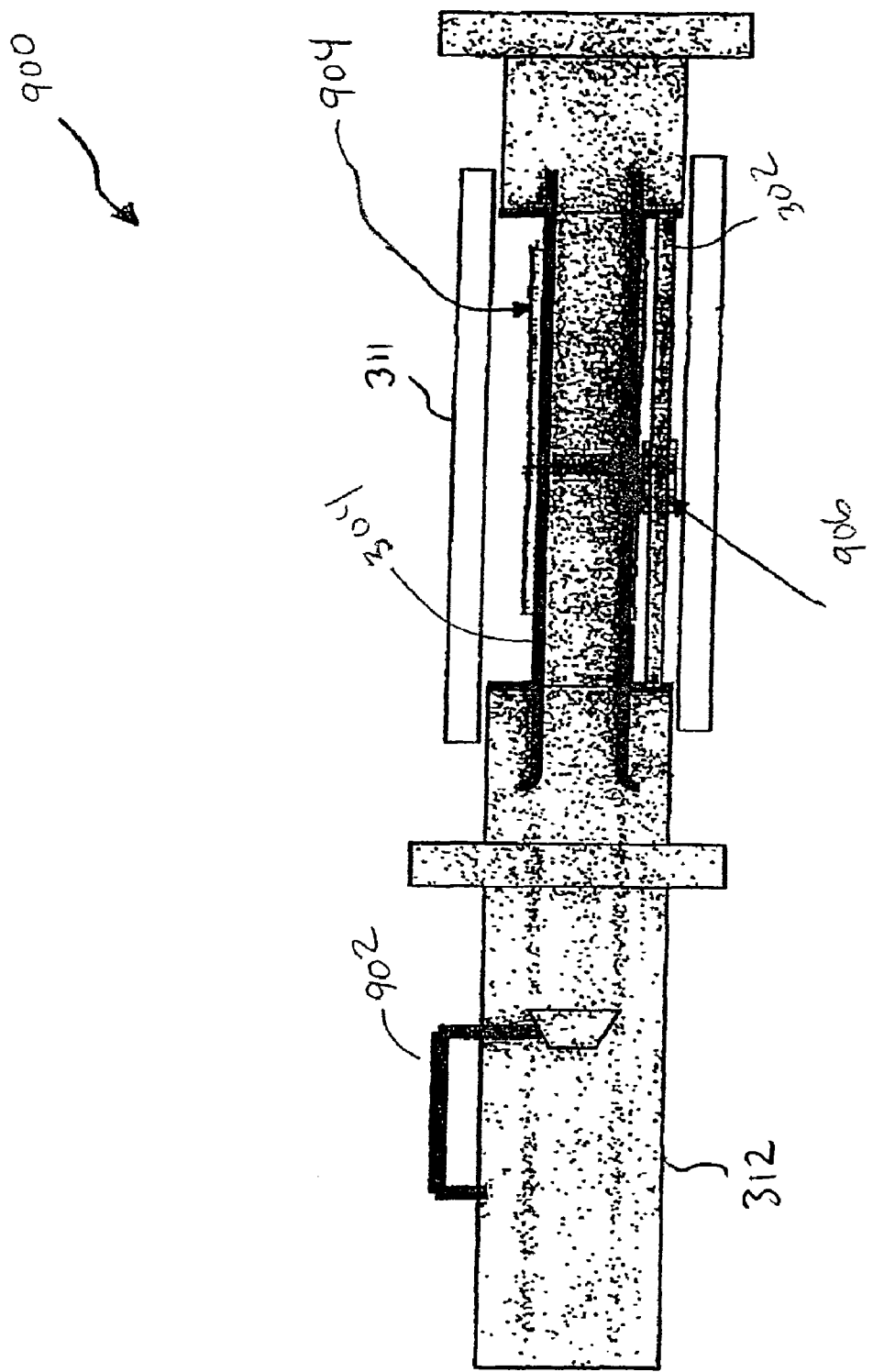
FIG. 27 illustrates a flow meter system having a bypass pipe to separate the fluid flow and measure parameters of a fluid flow including a multiphase fluid flow, in accordance with the present invention.

Referring to FIG. 27, an eighth embodiment 900 of the multi-phase flow meter is shown (excluding the processing unit) similar to the system 500 shown in FIG. 17. The meter 900 includes a DP meter 902 mounted to the pipe 312, while the other portion of the meter is a spool piece similar to that shown in FIG. 25 and including, a sonar flow meter 904, and a watercut meter 906. The flow system 900 also includes similar features as that shown in FIG. 26 for separating the liquid and gas portions of the flow. The bypass pipe 302 is shown as a straight pipe extending across the narrowed portion of the primary pipe 304. Furthermore, as is true for all the embodiments provided herein, the sensor portion of the present invention may be a spool piece having a pair of flanges disposed at opposing axial ends of the sensors portions. A cover 311 may be disposed over the narrowed portion of the primary pipe 304 to protect the meters disposed therein.

Figure 28:
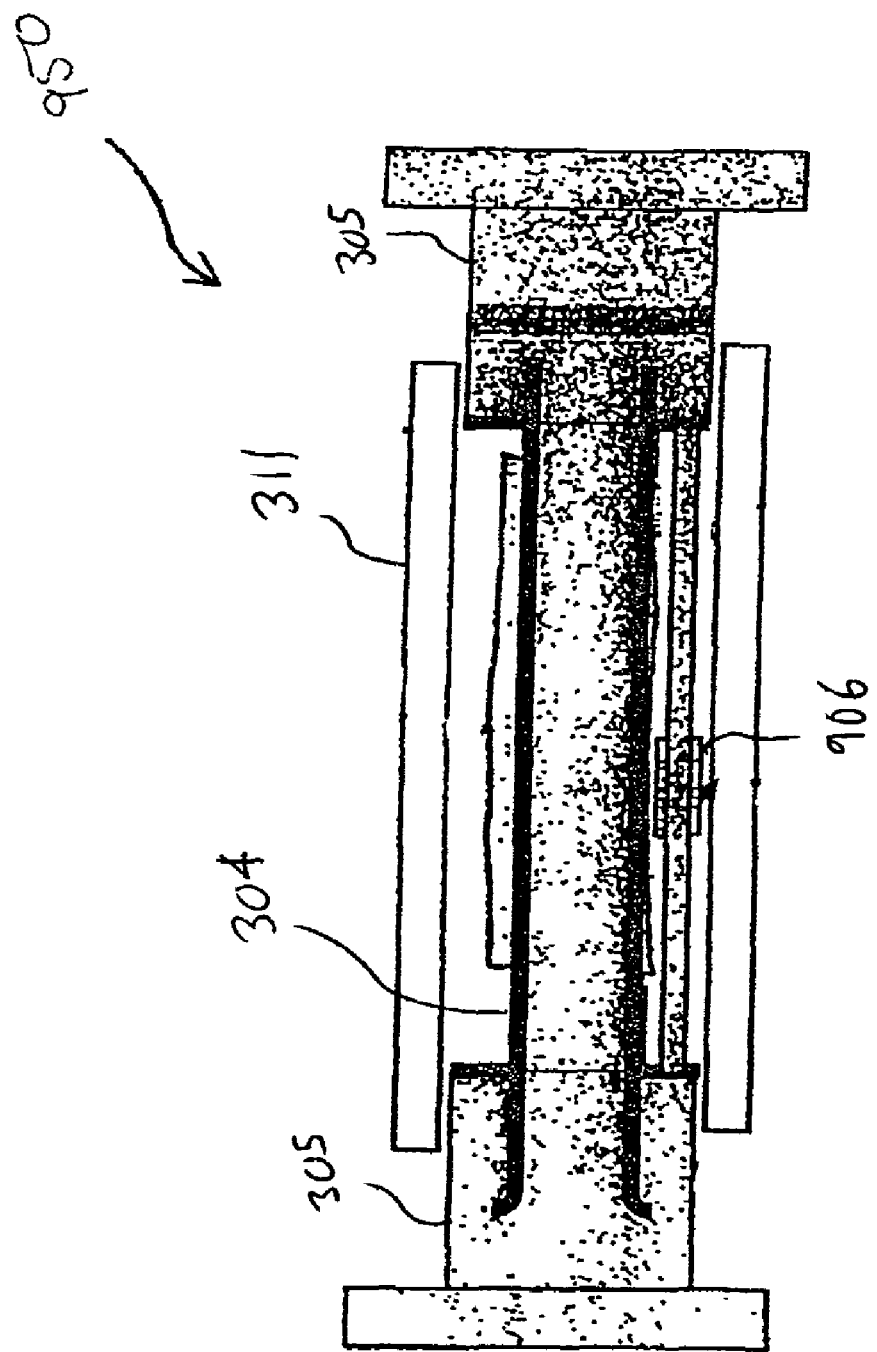
FIG. 28 illustrates a flow meter system having a bypass pipe to separate the fluid flow and measure parameters of a fluid flow including a multiphase fluid flow, in accordance with the present invention.

Referring to FIG. 28, a ninth embodiment 950 of the present invention similar to the system 900 shown in FIG. 27 is shown, wherein the system 950 does not include the DP meter. This system 950 provides a gas rate and water cut measurement similar to that described herein before.

Furthermore, referring to FIG. 29, a tenth embodiment 975 of the sensor portion of the present invention (excluding the processing unit) similar to the system 550 shown in FIG. 20 is shown, wherein the flow system 975 includes a DP meter 980, a sonar flow meter 985, a flow meter 990 (on the bypass pipe 502), and a watercut meter 995. The flow system 975 also includes similar features as that shown in FIGS. 26 and 28 for separating the liquid and gas portions of the flow. The system 975 measures the gas and liquid rate in the dryer gas stream flowing through the narrowed portion of the primary pipe 304, and the flow rate and the water cut in the bypass pipe 302. These measurements are combined to determine the overall rate and composition.

Referring to FIG. 30, a twelfth embodiment of the multiphase meter 1000 of the present invention is shown and includes a first pipe 1002 and a second pipe 1004, wherein the first pipe 1002 includes a first pipe diameter 1006 and the second pipe 1004 includes a second pipe diameter 1008, the first pipe diameter 1006 being larger than the second pipe diameter 1008. The first pipe 1002 and the second pipe 1004 are associated with each other such that at least a portion 1010 of the second pipe 1004 is extendingly disposed within the first pipe 1002 to form a primary flow channel 1003 traversing the first pipe 1002 and the second pipe 1004, as shown in FIG. 30. The portion 1010 of the second pipe 1004 disposed within the first pipe 1002 extends sufficiently far enough into the first pipe 1002 to form a bypass flow channel 1012 between the first pipe 1002 and the second pipe 1004. The portion 1010 of the second pipe 1004 includes a through hole 1014 which communicates the bypass flow channel 1012 with the primary flow channel 1003. A clean out or access port 1021 is provided having a plug 1023 to provide easy access to the bypass flow channel 1012, The sensor portion 1000 also includes a DP meter 1016 (including pressure sensors 1017), a water cut meter 1018 (including an ultrasonic sensor 1019) and a sonar base flow meter 1020.

As shown in FIG. 30, a fluid flow 100 (e.g., wet gas) is shown being introduced into the first pipe 1002. As the fluid flow 100 encounters the portion 1010 of the second pipe 1004 the gas portion 104 of the fluid flow 100 flows into the primary flow channel 1003 while the liquid portion 106 of the fluid flow 100 (having condensed on the inner walls of the pipe or settled to the bottom of the pipe) flows into the annular bypass flow channel 1012, exiting from the through hole 1014 and back into the primary flow channel 1003. The watercut meter 1018 analyzes the liquid portion 106 of the fluid flow 100 within the bypass flow channel 1012. As such, the bypass flow channel 1012 functions as a liquid leg as in the embodiments disclosed hereinabove.

As shown in FIGS. 30 and 31, the water cut meter 1018 is an ultrasonic sensor 1019 functioning in the pulse/echo mode as described hereinbefore to determine the water cut of the liquid portion 106. The ultrasonic sensor may be ported (or wetted) in the pipe 1002 or clamped onto the pipe 1002. The ultrasonic sensor is disposed to provide an ultrasonic signal perpendicular to the direction of the liquid 106 flow. A reflector 1028 may be provided or mounted to the opposing outer wall of the inner pipe 1010, as shown in FIG. 31.

Figure 32:
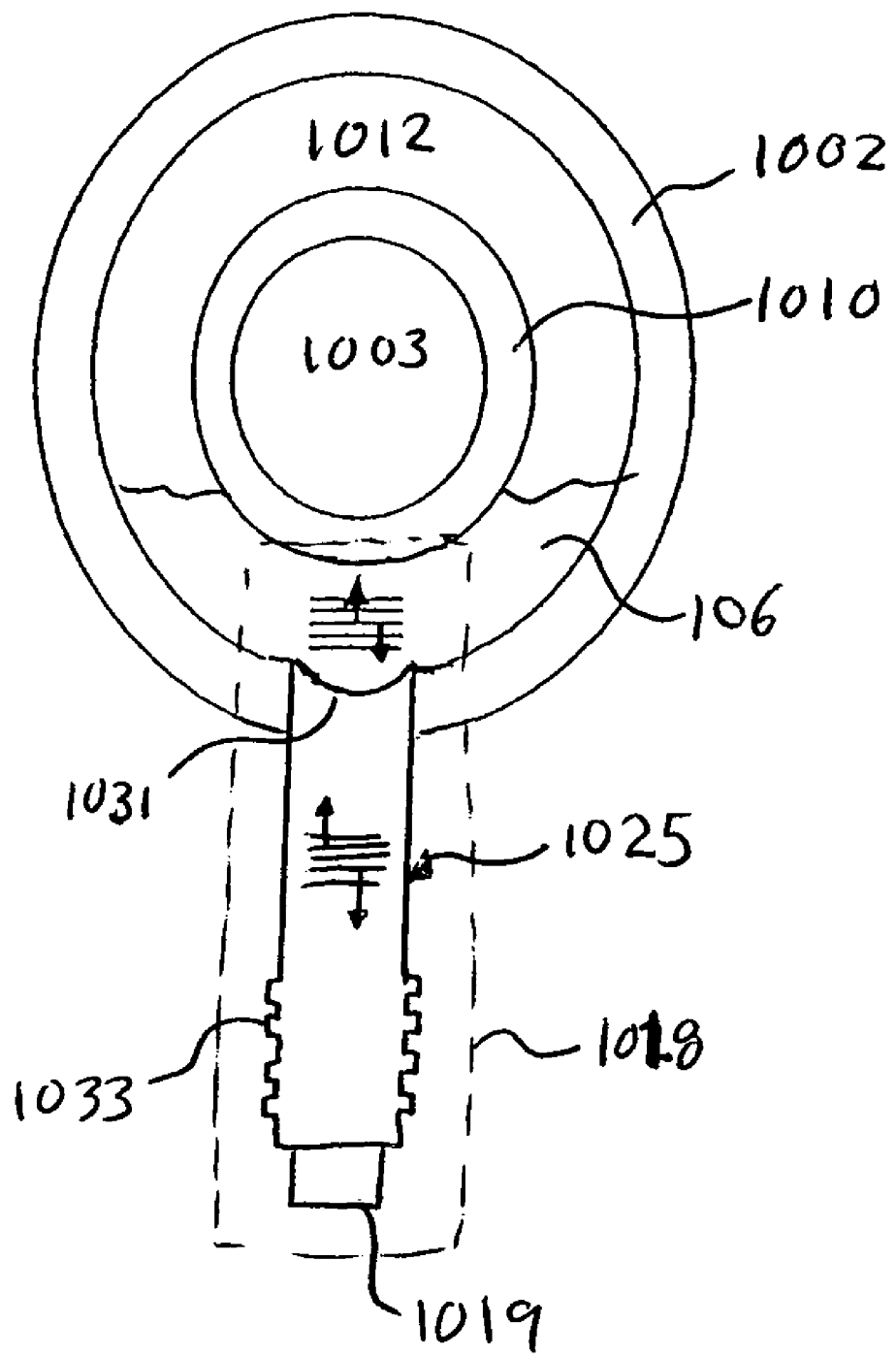
FIG. 32 is a cross-sectional view of another embodiment of the watercut sensor of FIG. 30, in accordance with the present invention.

FIG. 32 illustrates another embodiment of a watercut meter 28, similar to that shown in FIGS. 30 and 31. The watercut meter includes an ultrasonic sensor and a stand off 1025. The stand off is a rod formed of a metal material having a predetermined length. One end is welded or otherwise mounted through the outer pipe 1002 such that the end is wetted. The ultrasonic sensor 1019 is mounted to the other end. The sensor transmits and receives an ultrasonic sensor through the stand off 1025 and liquid 106. The present embodiment of the watercut is shown without the reflector 1028 of FIG. 31, however, the present invention contemplates using such a reflector in this embodiment. The standoff 1025 functions to attenuate, reduce or eliminate stray or alias reflections to provide a clean reflection of the desired reflection of the transmitted signal to more accurately measure the transit time of the signal, and hence the speed of sound of the liquid. The wetted end of the stand off 1025 includes a spherical or cup-shaped depression 1031 to focus the ultrasonic signal in the desired direction, as well as deflect unwanted reflections or scatter. While the depression 1031 is shown as being spherically shaped, one will appreciate that the depression may have any desirable shape to focus the ultrasonic signal and attenuate unwanted reflections/signals. The standoff 102 further includes annular threads (grooves) or protrusions 1033 extending radially from the standoff. The protrusions (or grooves) attenuate and/or delay unwanted reflections or scattered signals to further provide a cleaner return reflection to enable identification of the returned ultrasonic signal. The length of the standoff is selected to reduce or eliminate the other reflections that may return to the ultrasonic sensor at the same time.

While the water cut meter 1018 has been described as having an ultrasonic sensor 1019, it should be appreciated that the watercut may be determined via any water cut meter and/or probe suitable to the desired end purpose, such as the Redeye System, manufactured by Weatherford Corporation, which may be inserted through a hole in the outer wall 1002 for insertion within the bypass channel 1012. It should also be appreciated that the through hole 1014 may be sized as necessary and adjustably configurable for particular flows and/or applications as desired, to reduce clogging and ensure the bypass channel 1012 is full such that the level of the liquid is as high as the lower portion of the inner pipe 1010 to reduce or eliminate gas passing through the through hole 1024.

Moreover, the present invention contemplates that the sonar meter may be substituted with an ultrasonic sensor meter that uses any one of the following types of meters: Transit Time Ultrasonic Flow Meter (TTUF), Doppler Ultrasonic Flowmeter (DUF), and Cross Correlation Ultrasonic Flow Meter (CCUF), similar to that described in the article "Guidelines for the Use of Ultrasonic Non-Invasive Metering Techniques" by M. L. Sanderson and H. Yeung, published on Jul. 17, 2002, which is incorporated herein by reference. One such CCUF is the GE Panametrics DigitalFlow™ CTF878 flowmeter having a pair of ultrasonic sensors disposed axially along the pipe, which is incorporated herein by reference. It should also be appreciated that while the invention is discussed herein with reference to the Lockhardt-Martinelli Number and/or Liquid Mass Rates, other parameters related to wetness may also be used. It should be further appreciated that the method of the present invention provides for measurements that are very insensitive to wetness. As such, the present invention allows for a greater difference in the over reporting between the sonar meter and the DP meter which translates into measurements that have a greater accuracy and resolution than existing methods.

One will appreciate that while in the embodiments presented herein before do not measure the phase fraction of the oil and gas in the narrowed portion of the primary pipe for the liquid passing therethrough, the processing unit may assume that the oil/water ratio is similar to that measured in the bypass pipe using the watercut measurement to provide a more accurate measurement of the phase fraction and flow rate of each of the components of a multiphase fluid. Moreover, while the invention disclosed herein is discussed in terms of a DP meter(s), a sonar meter and/or an ultrasonic meter, the present invention contemplates that any meter and/or combination of meters suitable to the desired end purpose may be used, such that the meters provide an output measurement having a repeatable over report function (or output signal) with respect to the wetness of the flow, wherein the over reporting is substantially less than the over reporting of the DP meter. One should also appreciate that the meters (e.g., sonar meter and ultrasonic meter) may be combined with the differential meter and may also comprise non-invasive clamp on sensors or wetted sensors. It should be further understood that any of the features, characteristics, alternatives or modifications described regarding a particular embodiment herein may also be applied, used, or incorporated with any other embodiment described herein. Although the invention has been described and illustrated with respect to exemplary embodiments thereof, the foregoing and various other additions and omissions may be made therein and thereto without departing from the spirit and scope of the present invention.

The method of the invention may be embodied in the form of a computer or controller implemented processes. The invention may also be embodied in the form of computer program code containing instructions embodied in tangible media, such as floppy diskettes, CD-ROMs, hard drives, and/or any other computer-readable medium, wherein when the computer program code is loaded into and executed by a computer or controller, the computer or controller becomes an apparatus for practicing the invention. The invention can also be embodied in the form of computer program code, for example, whether stored in a storage medium, loaded into and/or executed by a computer or controller, or transmitted over some transmission medium, such as over electrical wiring or cabling, through fiber optics, or via electromagnetic radiation, wherein when the computer program code is loaded into and executed by a computer or a controller, the computer or controller becomes an apparatus for practicing the invention. When implemented on a general-purpose microprocessor the computer program code segments may configure the microprocessor to create specific logic circuits.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. An apparatus for determining a characteristic of a multiphase fluid flow within a pipe, which includes an upstream section and a downstream section, and a gas leg portion and a liquid leg portion, which portions extend between the upstream and downstream sections, the apparatus comprising:

a separating device for separating the fluid into a gas component and a liquid component and directing said gas component to flow within the gas leg portion of the pipe and said liquid component to flow within the liquid leg portion of the pipe;

a gas leg portion metering device, having a first metering element operative to determine a first value of a flow characteristic of the gas component, the first metering element having a first sensitivity to a wetness of the gas component, and a second metering element operative to determine a second value of the flow characteristic, the second metering element having a second sensitivity to the wetness of the gas component, wherein one of the first sensitivity and the second sensitivity is greater than the other;

a liquid leg portion metering device, wherein said liquid leg portion metering device generates liquid component data responsive to a liquid component characteristic; and a processing device communicated with the gas leg portion metering device and the liquid leg portion metering device, said processing device being configured to receive and process the first and second values of the gas component flow characteristic and the liquid component data to determine a characteristic of the fluid flow.

2. The apparatus of claim 1, wherein the first metering element is a differential pressure based flow meter and the second metering element is a sonar based flow meter.

3. The apparatus of claim 2, wherein said differential pressure based flow meter is at least one of an orifice based flow meter, a venturi meter, an elbow flow meter and a v-cone meter.

4. The apparatus of claim 2, wherein said sonar based flow meter includes a plurality of sonar based flow meters.

5. The apparatus of claim 2, further comprising a differential base flow meter associated with the pipe downstream section of the pipe.

6. The apparatus of claim 2, wherein said differential based flow meter is disposed in at least one of an upstream location and a downstream location from said sonar based flow meter.

7. The apparatus of claim 1, wherein said liquid leg metering device includes at least one of a flow meter, a watercut meter, a density meter and a Speed of Sound Meter.

8. The apparatus of claim 1, wherein the processing device is operative to determine at least one of a Gas Volume Fraction (GVF), a volumetric flow rate and a water cut value of the fluid flow, using the first and second values of the flow characteristic and the liquid component data.

9. The apparatus of claim 1, wherein the upstream section of the pipe has a first cross-sectional area, and the gas leg portion of the pipe has a second cross-sectional area, wherein the second cross-sectional area is less than the first cross-sectional area; and wherein the gas leg portion of the pipe extends a distance into the upstream section of the pipe and creates a separator region disposed between the gas leg portion of the pipe and the upstream section of the pipe; and wherein the liquid leg portion of the pipe connects with the separator region.

10. The apparatus of claim 2, wherein the differential pressure based flow meter has a first pressure sensor disposed to sense fluid flow within the upstream section of the pipe and a second pressure sensor disposed to sense fluid flow within the gas leg portion of the pipe, and the differential pressure based flow meter is thereby operative to sense a difference in pressure between fluid flow within the upstream section of the pipe and fluid flow within the gas leg portion of the pipe.

11. A method for analyzing a multiphase fluid flow within a pipe comprising the steps of:

separating the fluid flow from an upstream section of the pipe into a component flow within a gas leg portion of the pipe, and a liquid component flow within a liquid leg portion of the pipe, and recombining the component flows into a downstream section of the pipe;

sensing the gas component flow with a first meter operative to determine a first value of a gas component flow characteristic, the first meter having a first sensitivity to a wetness of the gas component;

sensing the gas component flow with a second meter operative to determine a second value of the gas component flow characteristic, the second meter having a second sensitivity to the wetness of the gas component, wherein one of the first sensitivity and the second sensitivity is greater than the other;

sensing the liquid component within the liquid leg portion to determine a liquid flow characteristic; and determining a flow rate of liquid within the gas component flow using the first and second values of the as component flow characteristic.

12. The method of claim 11, wherein the first meter is a differential pressure based flow meter and the second meter element is a sonar based flow meter.

13. The method of claim 11, wherein the liquid component is sensed using at least one of a flow meter, a watercut meter, a density meter and a Speed of Sound Meter.

14. The method of claim 11, further comprising the step of determining at least one of a Gas Volume Fraction (GVF), a volumetric flow rate and a water cut value of the fluid flow, using the first and second values of the flow characteristic and the liquid component data.

* * * * *